US012629252B2

(12) United States Patent
Edwards et al.

(10) Patent No.: US 12,629,252 B2
(45) Date of Patent: May 19, 2026

(54) FORMABLE MESH FOR CORRECTING BONE DEFECTS

(71) Applicant: SUNNYBROOK RESEARCH INSTITUTE, Toronto (CA)

(72) Inventors: Glenn Edwards, Toronto (CA); Oleh Antonyshyn, Etobicoke (CA); James Mainprize, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 922 days.

(21) Appl. No.: 17/041,303

(22) PCT Filed: Apr. 5, 2019

(86) PCT No.: PCT/CA2019/050419
§ 371 (c)(1),
(2) Date: Sep. 24, 2020

(87) PCT Pub. No.: WO2019/191850
PCT Pub. Date: Oct. 10, 2019

(65) Prior Publication Data
US 2021/0022868 A1      Jan. 28, 2021

Related U.S. Application Data

(60) Provisional application No. 62/653,745, filed on Apr. 6, 2018.

(51) Int. Cl.
*A61F 2/28*      (2006.01)
*A61F 2/00*      (2006.01)
*A61F 2/30*      (2006.01)

(52) U.S. Cl.
CPC .......... *A61F 2/2846* (2013.01); *A61F 2/0063* (2013.01); *A61F 2002/30433* (2013.01)

(58) Field of Classification Search
CPC .................. A61F 2/2846; A61F 2/0063; A61F 2002/30433; A61B 17/8061; A61B 17/8071; A61B 17/8085
See application file for complete search history.

(56) References Cited

U.S. PATENT DOCUMENTS

| | | | |
|---|---|---|---|
| 5,431,980 A | 7/1995 | Mccarthy | |
| 5,468,242 A | 11/1995 | Reisberg | |

(Continued)

FOREIGN PATENT DOCUMENTS

| | | | |
|---|---|---|---|
| CN | 105326554 A | 2/2016 | |
| DE | 102009026929 A1 | 12/2010 | |

(Continued)

OTHER PUBLICATIONS

Machine Translation of WO 2017061007, retrieved Sep. 7, 2023. (Year: 2023).*

(Continued)

*Primary Examiner* — Tracy L Kamikawa
(74) *Attorney, Agent, or Firm* — Aird & McBurney LP; Stephen Leonard

(57)      ABSTRACT

Formable mesh implants suitable for correcting bone implants are disclosed. A formable mesh may include a plurality of node plates that define a lattice, where connecting arms extend from each node plate. Each connecting arm associated with a given node plate connects with a plurality of adjacent connecting arms at a respective intermediate connection region, such that each connecting arm associated with the given node plate is connected to a different intermediate connection region, and such that neighboring node plates are indirectly connected through multiple connecting arms. At least a subset of the node plates may respectively include a screw-receiving aperture, and the intermediate connection regions may be absent of screw-receiving apertures. In another example embodiment, a formable mesh is (Continued)

disclosed in which each connecting arm of a given node plate connects with an adjacent node plate, where adjacent node plates are directly connected through at least two connecting arms.

25 Claims, 26 Drawing Sheets

(56)                References Cited

U.S. PATENT DOCUMENTS

| | | | |
|---|---|---|---|
| 5,690,631 | A | 11/1997 | Duncan et al. |
| 5,743,913 | A | 4/1998 | Wellisz |
| 5,752,958 | A | 5/1998 | Wellisz |
| 5,766,176 | A | 6/1998 | Duncan |
| 5,814,048 | A | 9/1998 | Morgan |
| 5,980,540 | A | 11/1999 | Bruce |
| 6,071,291 | A | 6/2000 | Forst et al. |
| 6,093,188 | A | 7/2000 | Murray |
| 6,206,883 | B1 | 3/2001 | Tunc |
| 7,662,155 | B2 | 2/2010 | Metzger et al. |
| 7,942,913 | B2 | 5/2011 | Ziolo et al. |
| 8,084,117 | B2 | 12/2011 | Lalvani |
| 8,298,286 | B2 | 10/2012 | Trieu |
| 8,298,292 | B2 * | 10/2012 | Swords ............... A61F 2/30965 |
| | | | 623/23.72 |
| 8,337,533 | B2 | 12/2012 | Raines et al. |
| 8,398,720 | B2 | 3/2013 | Swords |
| D694,886 | S | 12/2013 | Jagger et al. |
| D751,202 | S | 3/2016 | Gabele |
| 9,549,819 | B1 | 1/2017 | Bravo et al. |
| D815,741 | S | 4/2018 | Schuldt-Hempe et al. |
| 2005/0261780 | A1 | 11/2005 | Heino et al. |
| 2005/0288790 | A1 | 12/2005 | Swords |
| 2006/0224242 | A1 | 10/2006 | Swords et al. |
| 2007/0213838 | A1 | 9/2007 | Hengelmolen |
| 2009/0099409 | A1 | 4/2009 | Luehrs et al. |
| 2009/0210008 | A1 * | 8/2009 | Butler ................ A61B 17/7059 |
| | | | 606/280 |
| 2009/0216338 | A1 | 8/2009 | Gingras et al. |
| 2010/0145386 | A1 * | 6/2010 | Greenhalgh ....... A61B 17/8863 |
| | | | 606/279 |
| 2011/0282452 | A1 | 11/2011 | Koerner et al. |
| 2011/0301717 | A1 | 12/2011 | Becker |
| 2012/0330435 | A1 | 12/2012 | Engqvist et al. |
| 2013/0103079 | A1 | 4/2013 | Lau et al. |
| 2013/0236853 | A1 | 9/2013 | Axelsson et al. |
| 2014/0114266 | A1 | 4/2014 | Arcand |
| 2014/0276995 | A1 | 9/2014 | Lau et al. |
| 2015/0105806 | A1 | 4/2015 | Dorafshr et al. |
| 2015/0250574 | A1 | 9/2015 | Egnelov |
| 2015/0374497 | A1 * | 12/2015 | Engstrand ................. A61F 2/28 |
| | | | 623/17.19 |
| 2017/0143872 | A1 | 5/2017 | Limem et al. |
| 2017/0238981 | A1 * | 8/2017 | Madjarov .......... A61B 17/8076 |

FOREIGN PATENT DOCUMENTS

| | | |
|---|---|---|
| EP | 0433852 B1 | 3/1996 |
| EP | 2030596 A1 | 4/2009 |
| JP | 201446025 A | 3/2014 |
| KR | 100952730 B1 | 4/2010 |
| WO | 2008047415 A1 | 4/2008 |
| WO | 2012036129 A1 | 3/2012 |
| WO | 2012079611 A1 | 6/2012 |
| WO | 2016024248 A1 | 2/2016 |
| WO | WO-2017061007 A1 * | 4/2017 ......... A61B 17/8061 |

OTHER PUBLICATIONS

Bioplate Product Brochure, Bioplate, 2015.
CranioCurve Product Brochure, CranioCurve, 2015.
Biomesh Product Brochure, Biomesh, 2015.
Mikami et al., "Exposure of titanium implants after cranioplasty: A matter of long-term consequences", Inter. Neuro. Adv. Tech. and Case Mgmt. 8, 64-67 (2017).
Lau et al, "A Method for Combining Thin and Thick Malleable Titanium Mesh in the Repair of Cranial Defects", Cureus 7, e267, 2015.
International Search Report for PCT/CA2019/050419 dated Jul. 11, 2019.

* cited by examiner

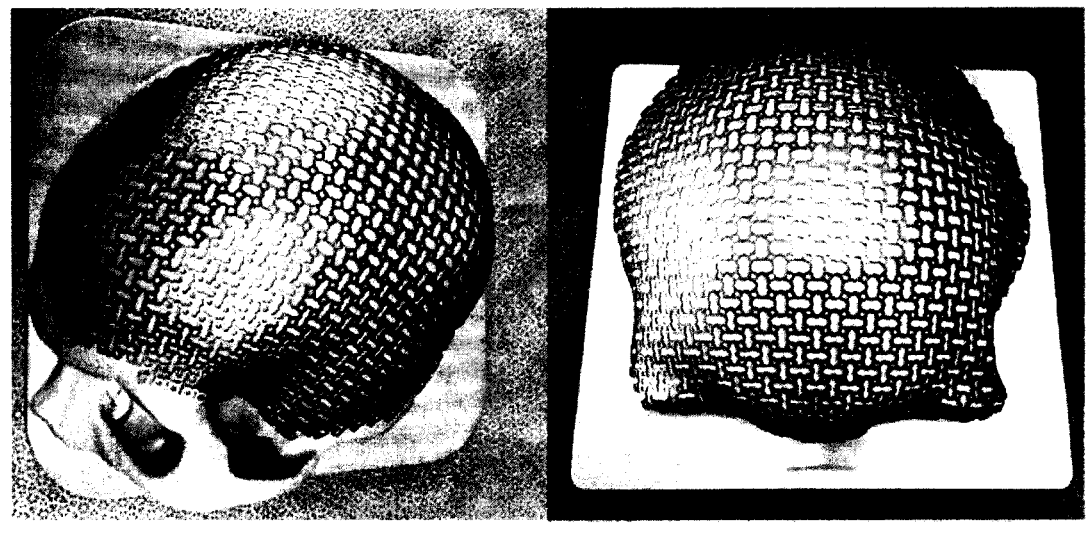
FIG. 1A                    FIG. 1B
FIG. 1C
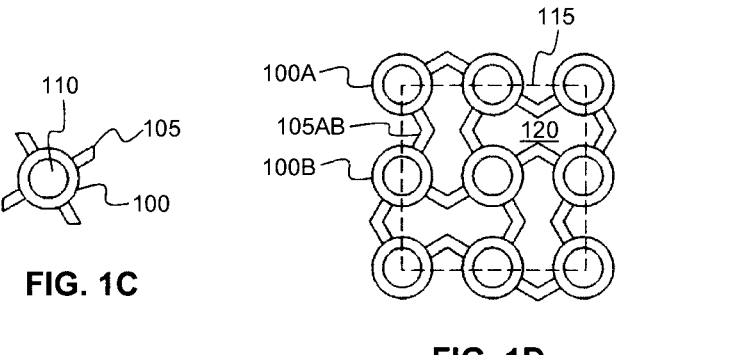
FIG. 1D                    FIG. 1E

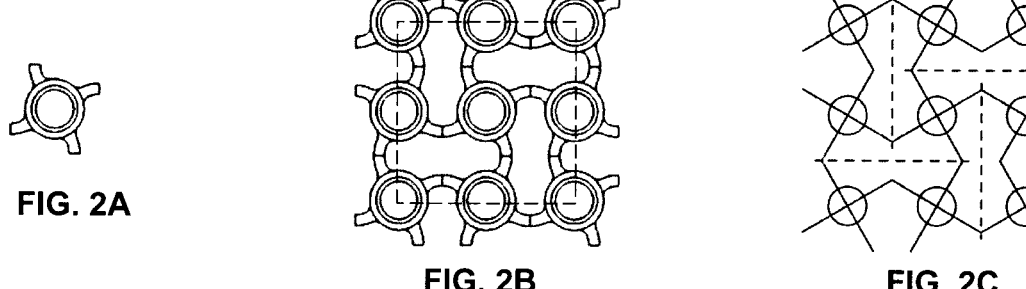
FIG. 2A
FIG. 2B
FIG. 2C
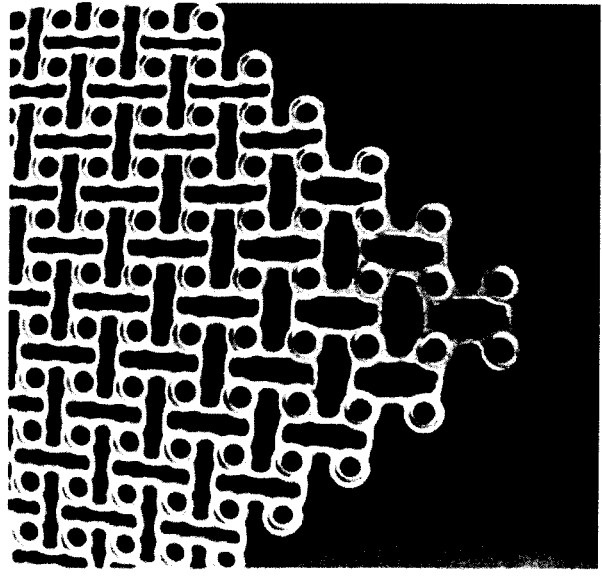
FIG. 2D

FIG. 7G
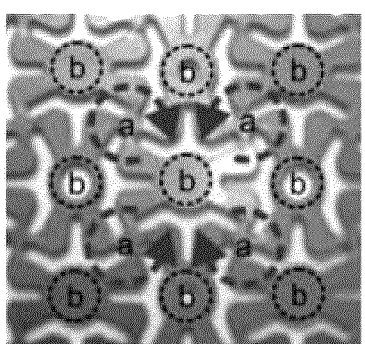
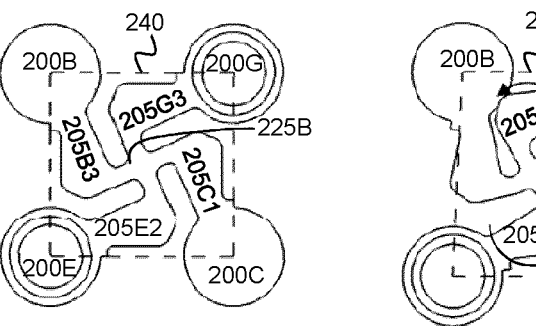
FIG. 7H          FIG. 7I
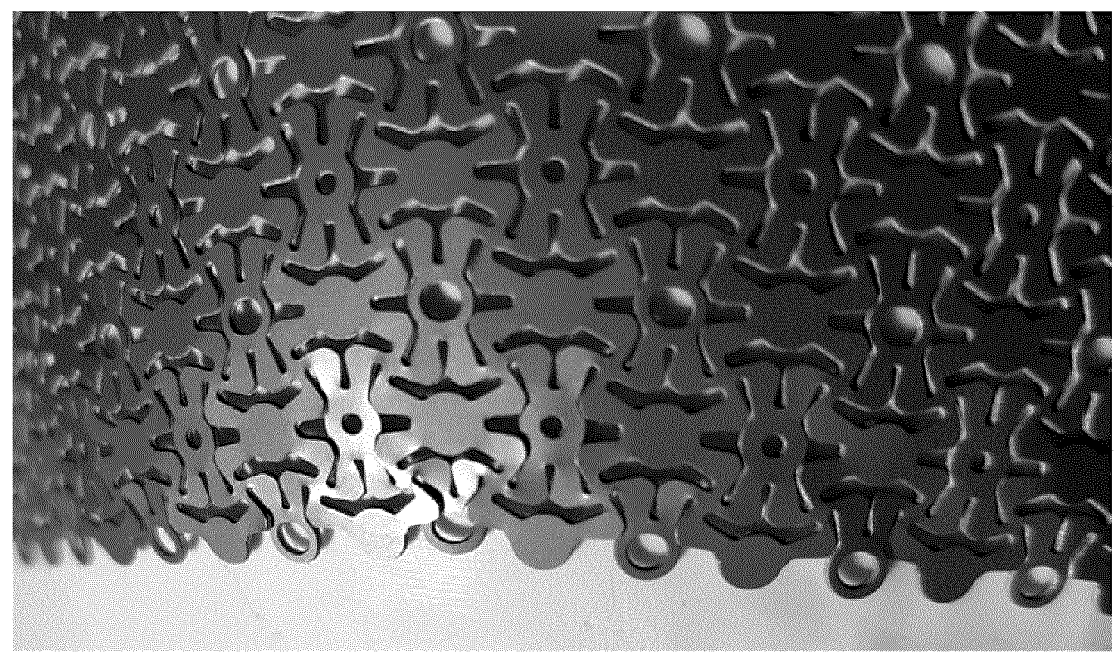
FIG. 7J

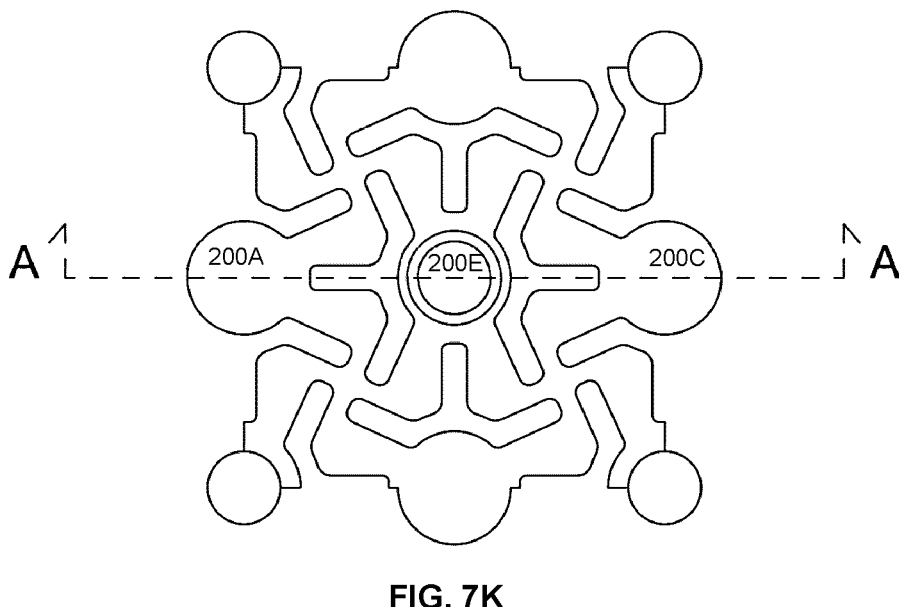
FIG. 7K
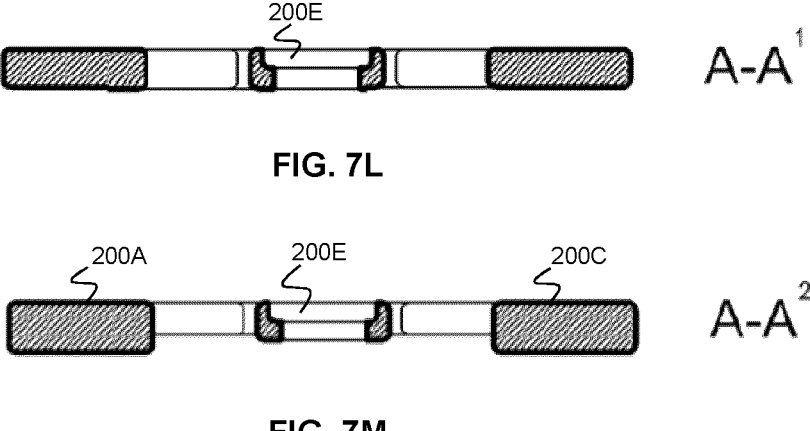
FIG. 7L
FIG. 7M

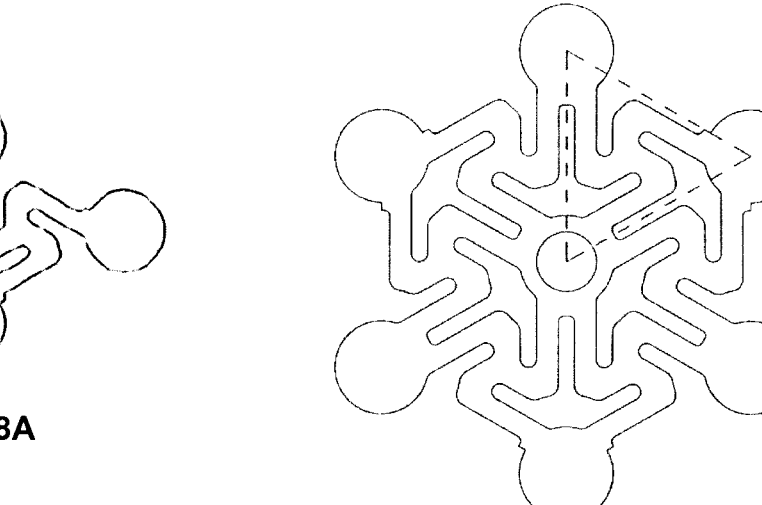
FIG. 8A
FIG. 8B
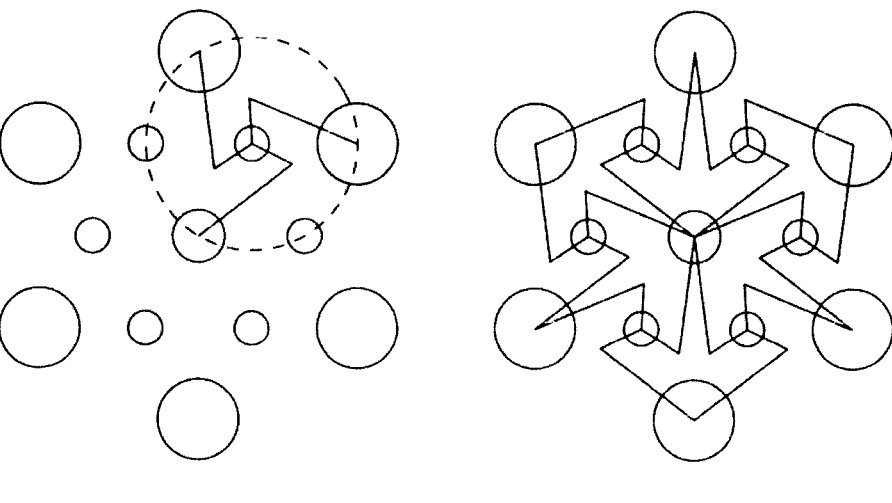
FIG. 8C             FIG. 8D

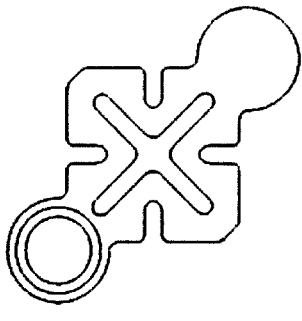
FIG. 10A
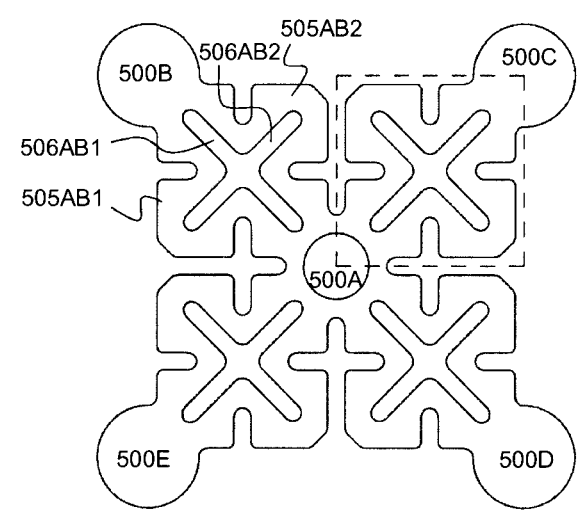
FIG. 10B
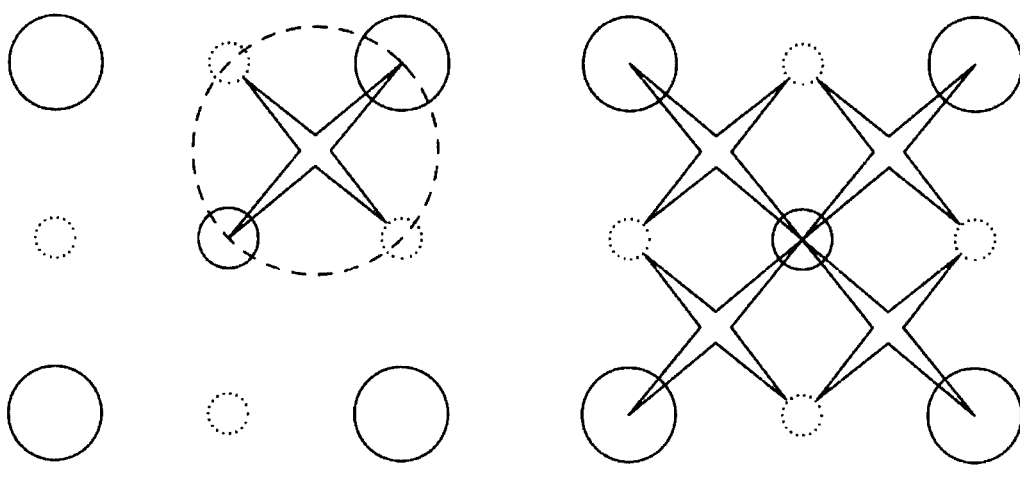
FIG. 10C                    FIG. 10D

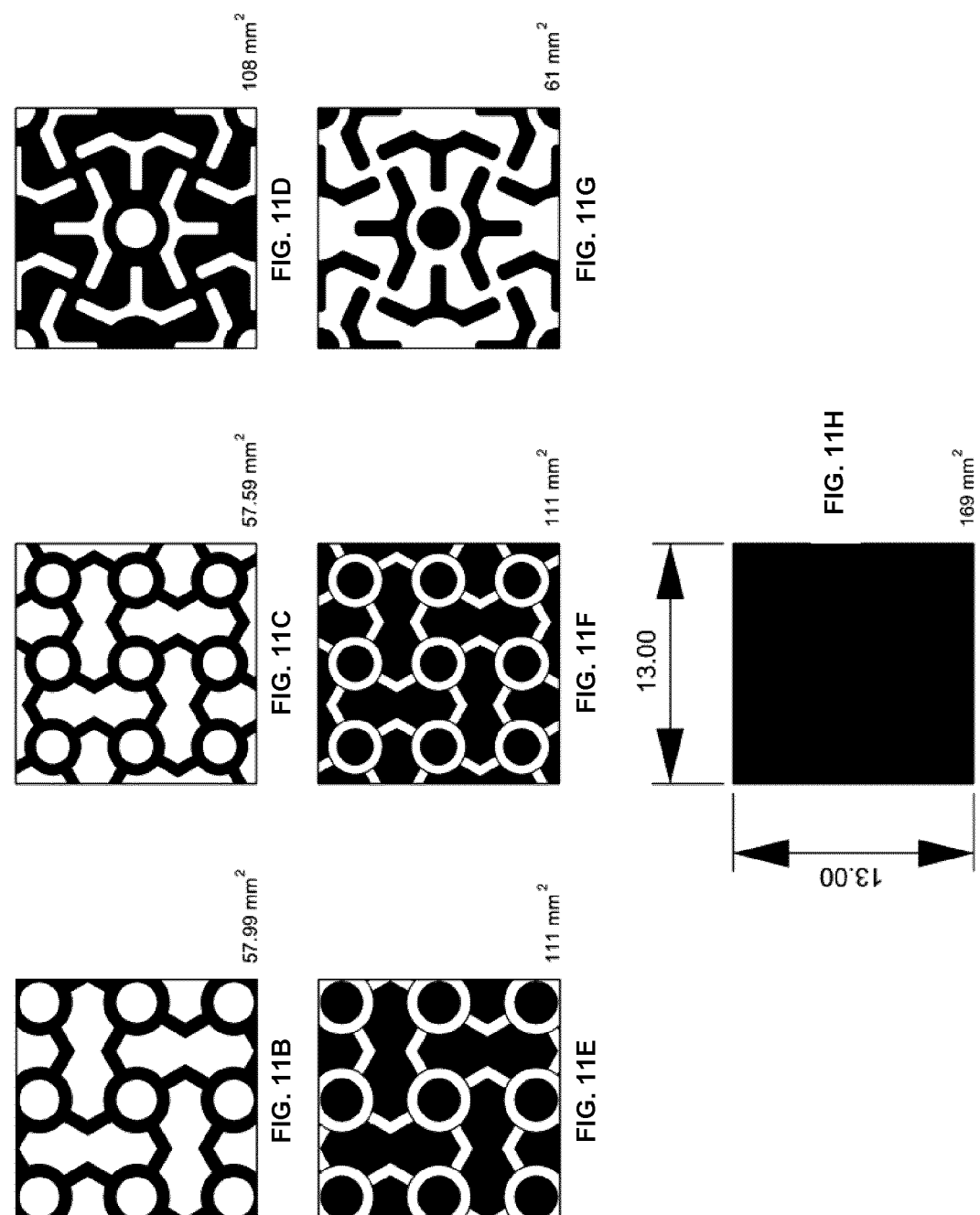

FORMABLE MESH FOR CORRECTING BONE DEFECTS

This application is a National Phase application claiming the benefit of the international PCT Patent Application No. PCT/CA2019/050419, filed on Apr. 5, 2019, in English, which claims priority to U.S. Provisional Patent Application No. 62/653,745, titled "FORMABLE MESH FOR CORRECTING BONE DEFECTS" and filed on Apr. 6, 2018, the entire contents of which are incorporated herein by reference.

BACKGROUND

The present disclosure relates to implants for correcting bone defects.

The surgical repair of a defect of the skull or facial bones can be a technically difficult, laborious and time-consuming procedure. Accurate restoration of the missing anatomy is particularly challenging. The recent adaptation of computer assisted design and rapid prototyping technology is known to dramatically increase efficiency and improve outcomes. Provided that the defect is stable, clearly defined and well visualized prior to surgery, computer modeling can be employed to generate a virtual 3D model of a patient-specific implant.

Titanium mesh has proven to be effective clinically in the reconstruction of non-load-bearing defects of the skull and facial bones (Kuttenberger and Hardt, J. CranioMaxfac. Surg., 2001; Schipper et al., Eur. Arch. Otorhinolaryngol., 2004). The mesh provides a stable, permanent, biocompatible reconstruction which is well tolerated, even when in direct contact with paranasal sinuses. Titanium is the most biocompatible metal and is known to generate a minimal inflammatory response when implanted. Titanium becomes osseointegrated after implantation and is well tolerated even in a contaminated field. Due to its non-ferromagnetic properties, titanium is compatible with magnetic resonance imaging, and generates minimal artifacts in magnetic resonance imaging (MRI) images. CT (computed tomography) artifact associated with titanium mesh is also negligible and postoperative visualization of structures adjacent to titanium mesh is unobstructed. Titanium mesh is exceptionally versatile under a variety of clinical scenarios and can be readily adapted to virtually any non-load bearing craniofacial defect. The mesh pattern is porous, allowing free drainage of body fluids and minimizing complications associated with fluid retention in closed spaces (hematoma, seroma, etc.). The mesh is partially transparent, facilitating visualization of underlying structures through the mesh intraoperatively. Most importantly, titanium meshes are readily deformable. They are specifically designed to allow shaping into a three-dimensional construct, which can be done manually or using a mold system. They can be further trimmed to any required size for implantation. Conventional mesh designs also provide multiple locations for screw fixation.

Despite the aforementioned benefits of titanium meshes, conventional mesh designs have a number of associated drawbacks. Some of these are technical, posing challenges for the surgeon during intraoperative preparation of the implant, while some can have an adverse effect on patient outcomes and are far more significant. For example, the manual shaping of a conventional titanium sheet into a three-dimensional shape can be challenging. The difficulty increases with the complexity of surface topography and underlying anatomy. Contouring over more defined regions with acute angles results in loss of surface fidelity and buckling of titanium mesh connecting arms. Furthermore, the trimming of conventional meshes necessarily results in a corrugated implant margin with irregular sharp barbs. These can lacerate or impinge abutting soft tissues and potentially restrict mobility of specific soft tissues such as extraocular muscles within the orbit. The implant edge is often palpable and visible for patients with thin skin.

Moreover, in order to be malleable, conventional mesh designs require large open space voids between connecting arms, resulting in a very low "fill factor", the surface area ratio between solid mesh and void space. These voids pose three problems. Firstly, the presence of large voids precludes the use of meshes in areas where soft tissue prolapse through mesh voids causes functional impairment. This is particularly important in orbital cavity reconstruction, where prolapse of intraorbital septa or extraocular muscles through the mesh can potentially result in extraocular muscle motility disorders. Secondly, adhesions between soft tissues on either side of the mesh unnecessarily complicate implant removal. The large voids allow soft tissues on either side of the mesh to "fuse" during healing. If implant removal is required for some indication, the surgery requires extensive dissection and separation of the adhesions. Risks of inadvertent injury to surrounding structures, hemorrhage, etc. are significant. Finally, the open mesh pattern with large voids also predisposes to late erosion of overlying soft tissues with implant exposure. Titanium mesh exposure is a recognized complication and has been documented in 16% of patients undergoing titanium cranioplasty. It has also been documented in dentoalveolar and maxillary reconstructions. This complication has particularly significant consequences, as it necessitates additional reconstructive surgery to remove the titanium implant and provide an alternative complex reconstruction. In a recent CT review of titanium mesh cranioplasty, thinning of overlying soft tissues (atrophy of skin, fat and muscle over the mesh) was demonstrated to occur in 44% of patients. This phenomenon is not observed in smooth, solid implants.

Conventional mesh designs are also known to exhibit low impact tolerance when compared to the skull or to other materials, such as PEEK.

FIGS. 1A-1G, 2A-2D, 3A-3D, 4A-4C, 5A-5D show various conventional mesh designs. FIGS. 1A-1G show a mesh developed by Stryker (henceforth referred to as the Stryker mesh). FIGS. 1A and 1B show two different view of the Stryker mesh formed onto a cranial mold. As can be seen in FIG. 1C, the fundamental structure of the Stryker mesh includes a node plate 100 having a set of four radiating connecting arms 105, where the node plate 100 has a central screw-receiving aperture 110. As can be seen in FIGS. 1A and 1B, the screw receiving aperture 110 is formed in every node plate of the mesh. FIG. 1D shows detail view of the Stryker mesh, showing a unit cell 115. The global mesh pattern is created by translating the geometry of the basic node and connecting arm configuration shown in FIG. 1D.

It is readily apparent from the mesh design shown in FIG. 1D that every node plate 100 is connected to its neighboring node plates via a single bent connecting arm. For example, node plates 100A and 100B are connected via the single connecting arm 105AB. A geometrical representation of the relationship between the nodes and the connecting arms is shown in FIG. 1E.

The Stryker mesh is sparsely filled by the node plates and connecting arms, leaving a large number of void regions 120. When the mesh is trimmed by cutting a set of connecting arms, the large voids result in a sharp and burred mesh periphery, as evidence in FIG. 1F. As noted above, the presence of such sharp peripheral regions is a significant drawback of such conventional mesh designs, as they result in a corrugated edge in the final construct that is palpable and visible for patients with thin skin.

The void regions are also easily distorted, via the deformation of the connecting arm 105, when compression and/or expansion forces are applied to the mesh. FIG. 1G shows the effect of deformation on the void regions, demonstrating the buckling of the mesh and significant expansion of the void regions—and the resulting local weakness of the mesh due to reduced fill factor—that can occur in areas of high curvature.

FIGS. 2A-2C illustrate another conventional mesh design (developed by Synthes, henceforth referred to as the Synthes mesh). As can be seen by comparing FIG. 2C and FIG. 1E, this mesh design is geometrically similar to the Stryker mesh design. FIG. 2D shows the significant expansion of the void regions when the Synthes mesh is deformed under stress.

FIGS. 3A-3C illustrate yet another conventional mesh design (developed by Bioplate, henceforth referred to as the Bioplate mesh). As can be seen by comparing FIG. 3C and FIG. 1E, this mesh design is a hexagonal lattice variation of the Stryker mesh design. FIG. 3D shows the significant expansion of the triangular void regions when the Bioplate mesh is deformed under stress.

FIGS. 4A-4C illustrate yet another conventional mesh design (developed by KLS, henceforth referred to as the KLS1 mesh). As can be seen by comparing FIG. 4C and FIG. 1E, this mesh design is a square lattice variation of the Stryker mesh design.

FIGS. 5A-5C illustrate yet another conventional mesh design (also developed by KLS, henceforth referred to as the KLS2 mesh). As can be seen by comparing FIG. 5B and FIG. 4B, this mesh design is a variation of KLS1 square lattice design in which the connecting arms have two bends. FIG. 5D shows the significant expansion of the void regions when the KLS2 mesh is deformed under stress, where deformation of the lattice is enhanced via the increased length of the connecting arms of the KLS2 mesh design relative to the KLS1 mesh design.

Each of the mesh designs described above different levels of formability and adaptability, based on the specific mesh pattern. It is noted that each of the representative mesh designs shown above share two common properties: (i) each node plate of each mesh has a screw-receiving aperture, and (ii) each node plate of each mesh is directly connected to a neighboring node plate via a single connecting arm.

The preceding example conventional mesh designs all share the following problems and design limitations: (i) undesirable gaps (void regions), especially after deformation, (ii) undesirable buckling of mesh links, (iii) palpable contour defects due to mesh thickness and/or open pattern, (iii) skin erosion due to large gaps, (iv) low impact resistance, (v) and connecting arms that do not bend to a contour properly when the mesh is formed to patient anatomy.

FIG. 6 is a photograph of a solid titanium implant. While the solid implant avoids some of the disadvantages associated with a mesh implant, it prohibits intraoperative viewing of the underlying tissue, and also is less formable under pressure than a mesh and is difficult to trim.

SUMMARY

Formable mesh implants suitable for correcting bone implants are disclosed. A formable mesh may include a plurality of node plates that define a lattice, where connecting arms extend from each node plate. Each connecting arm associated with a given node plate connects with a plurality of adjacent connecting arms at a respective intermediate connection region, such that each connecting arm associated with the given node plate is connected to a different intermediate connection region, and such that neighboring node plates are indirectly connected through multiple connecting arms. At least a subset of the node plates may respectively include a screw-receiving aperture, and the intermediate connection regions may be absent of screw-receiving apertures. In another example embodiment, a formable mesh is disclosed in which each connecting arm of a given node plate connects with an adjacent node plate, where adjacent node plates are directly connected through at least two connecting arms.

Accordingly, in one aspect, there is provided a formable implant for skeletal fixation or correction of skeletal defects, the formable implant comprising a formable mesh, the formable mesh comprising:

a plurality of node plates defining a lattice, wherein at least a subset of the node plates comprises respective screw-receiving apertures for receiving mounting screws therethrough;

each node plate having a plurality of connecting arms extending therefrom;

each connecting arm of the plurality of connecting arms associated with a given node plate extending to connect with a plurality of adjacent connecting arms at a respective intermediate connection region, each adjacent connecting arm being respectively associated with a different neighboring node plate, such that each connecting arm of the plurality of connecting arms associated with the given node plate is connected to a different intermediate connection region, and such that neighboring node plates are indirectly connected through multiple connecting arms; and wherein each intermediate connection region is absent of a screw-receiving aperture.

In another aspect, there is provided a formable implant for skeletal fixation or correction of skeletal defects, the formable implant comprising a formable mesh, the formable mesh comprising:

a plurality of node plates defining a lattice, wherein at least a subset of the node plates comprise respective screw-receiving apertures for receiving mounting screws therethrough;

each node plate having a plurality of connecting arms extending therefrom, each connecting arm of a given node plate connects with an adjacent node plate;

wherein adjacent node plates are directly connected through at least two connecting arms.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1A and 1B show photographs of an example of a titanium mesh known in the art.

FIG. 1C illustrates a unit cell of the mesh shown in FIG. 1A.

FIGS. 1D and 1E show an illustration of the mesh shown in FIG. 1A, and a schematic showing the respective nodes and connecting arms of the design, respectively.

FIG. 2A illustrates a unit cell of another mesh known in the art.

FIGS. 2B and 2C show an illustration of the mesh based on the unit cell of FIG. 2A, and a schematic showing the respective nodes and connecting arms of the design, respectively.

FIG. 2D is a photograph showing deformation of the mesh shown in FIG. 2B.

FIG. 7G is a detail of the photograph shown in FIG. 7F, annotated to show the rotation of the connecting arms about the intermediate connection regions under deformation.

FIGS. 7H and 7I illustrate the rotation of the connecting arms about the intermediate connection regions under deformation.

FIG. 7J is a photograph of the example mesh of FIG. 7F, demonstrating the overlapping of adjacent mesh elements under deformation of the mesh.

FIG. 7K shows an example unit cell of the mesh shown in FIG. 7A, 7P.

FIGS. 7L and 7M show cross-sectional views of the mesh unit cell shown in FIG. 7K, where the thickness of the mesh varies within the unit cell.

as shown in FIGS. 7K, 7L and 7M). It does not include any secondary holes.

FIG. 8A illustrates the intersection of connecting arms associated with different node plates at an intermediate connection region for a mesh having hexagonal symmetry.

FIG. 8B illustrates a unit cell of the hexagonal mesh shown in FIG. 8A.

FIGS. 8C and 8D schematically show the connection paths, via the connecting arms, among node plates of the mesh, for the mesh regions illustrated in FIGS. 8A and 8B, respectively.

FIG. 9F shows the intersection of connecting arms associated with different node plates at an intermediate connection region and FIG. 9G illustrates a unit cell of the mesh.

FIG. 10A illustrates the connection of different node plates via multiple connecting arms for an example square mesh.

FIG. 10B illustrates a unit cell of the mesh shown in FIG. 10A.

FIGS. 10C and 10D schematically show the connection paths, via the connecting arms, among node plates of the mesh, for the mesh regions illustrated in FIGS. 10A and 10B, respectively.

FIGS. 11B-11H show the mesh fill factor of various different mesh designs.

FIG. 14A shows left and right patterns for orbital floors that include both lateral and medial walls, and FIG. 14B shows left and right patterns for orbital floor and medial wall only.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As noted above, conventional bone fixation mesh designs suffer from a number of drawbacks, including undesirable gaps (void regions), especially after deformation; undesirable buckling of mesh links; palpable contour defects due to mesh thickness and/or open pattern; skin erosion due to large gaps; low impact resistance; and connecting arms that do not bend to a contour properly when the mesh is formed to patient anatomy. The present inventors sought to design a new mesh pattern that would overcome these limitations.

Figure 1F:
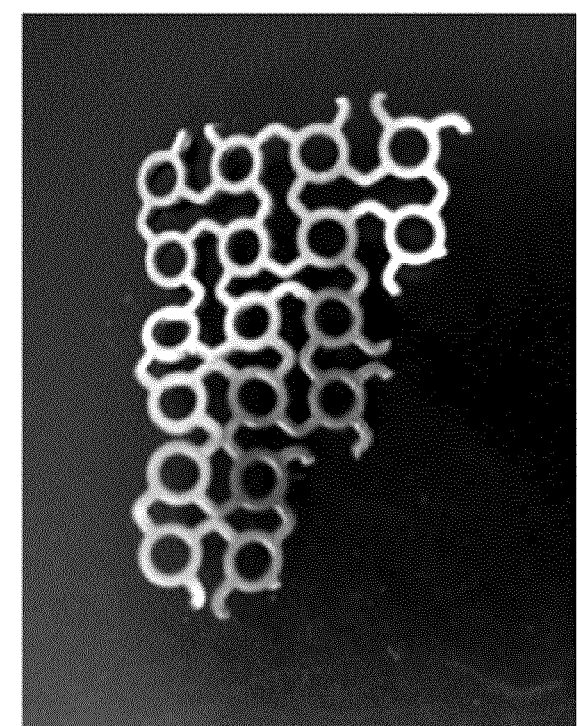
FIGS. 1F and 1G are photographs showing deformation of the mesh shown in FIG. 1A.
Figure 1G:
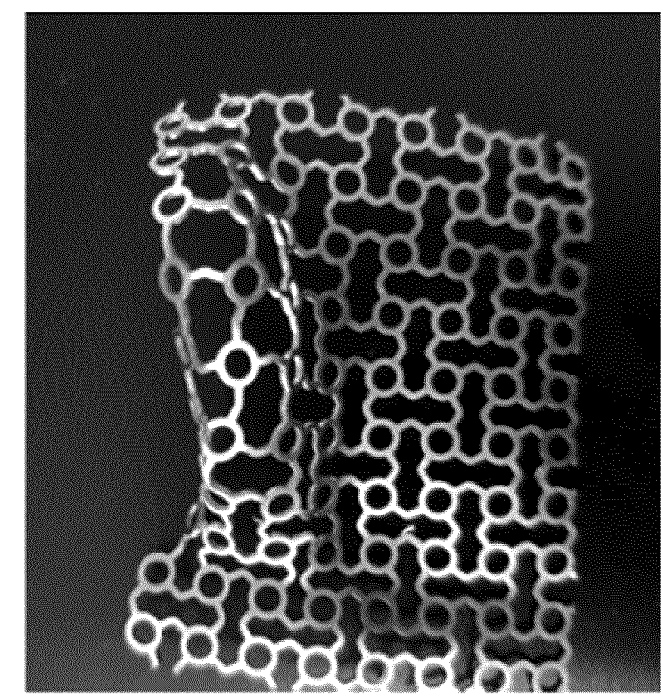
Figure 3A:
FIG. 3A illustrates a unit cell of yet another mesh known in the art.
Figure 3B:
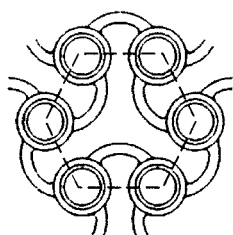
FIGS. 3B and 3C show an illustration of the mesh based on the unit cell of FIG. 3A, and a schematic showing the respective nodes and connecting arms of the design, respectively.
Figure 3C:
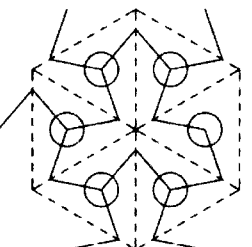
Figure 3D:
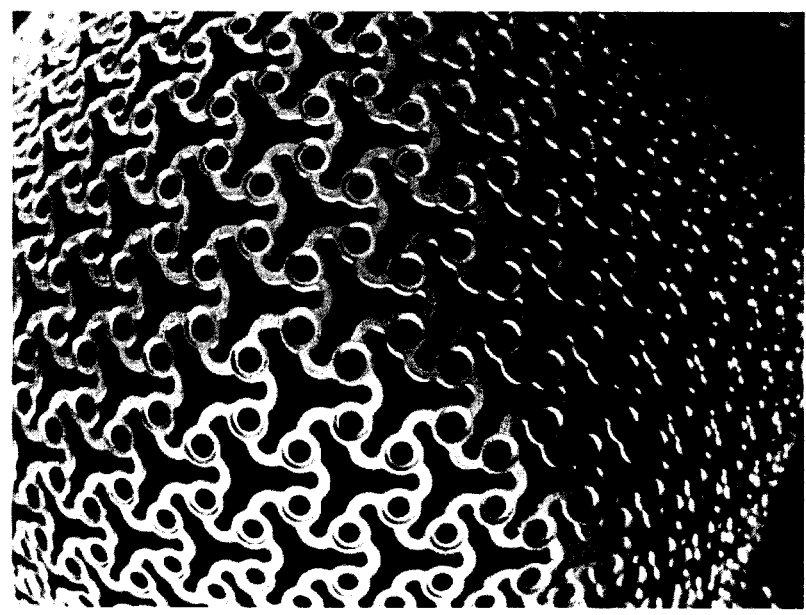
FIG. 3D is a photograph showing deformation of the mesh shown in FIG. 3B.
Figures 4A, 4B, 4C, 5A, 5B, 5C, 5D:
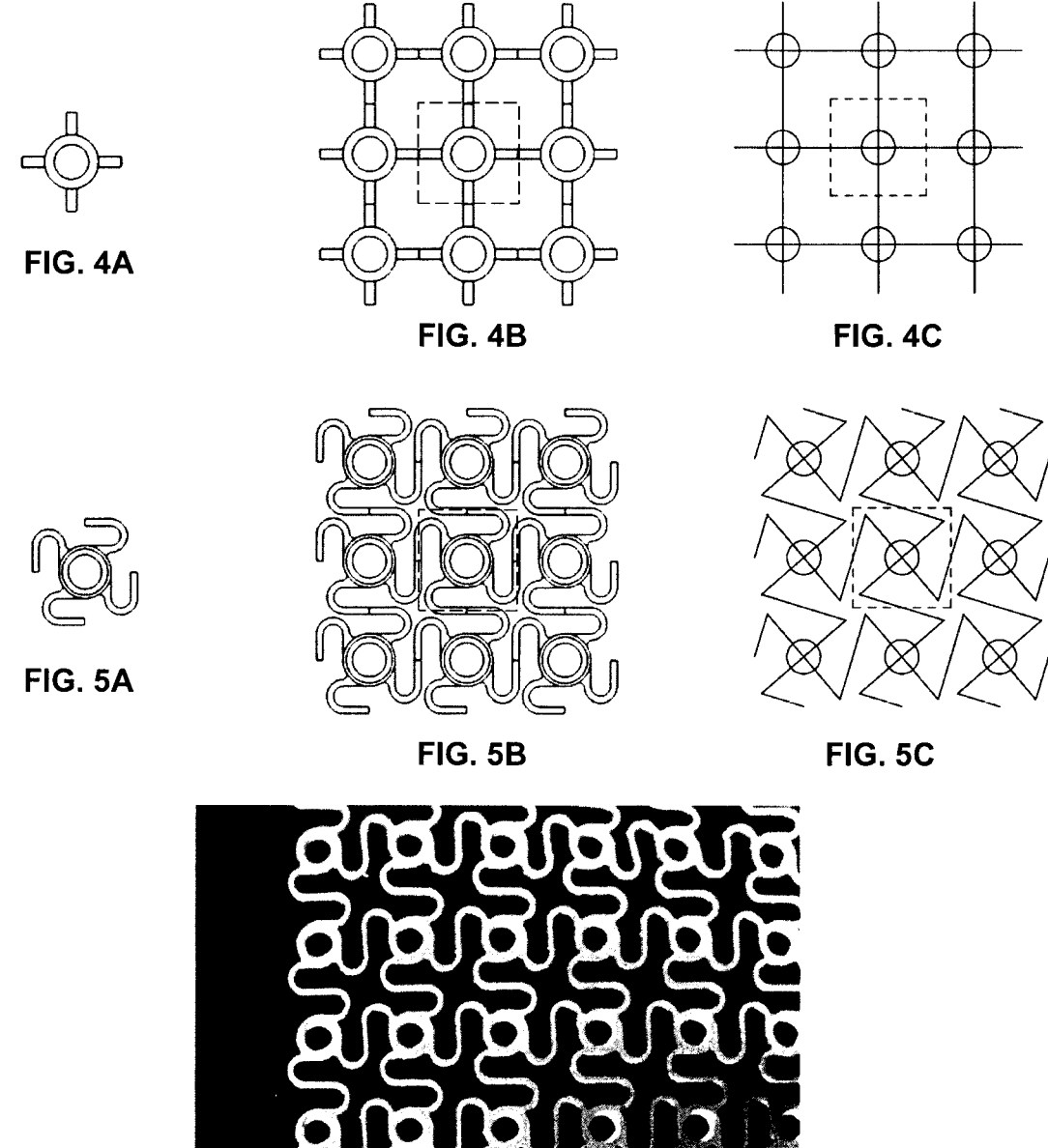
FIGS. 4A, 4B and 4C illustrate another conventional mesh design (developed by KLS, henceforth referred to as the KLS1 mesh).
FIG. 5A illustrates a unit cell of yet another mesh known in the art.
FIGS. 5B and 5C show an illustration of the mesh based on the unit cell of FIG. 5A, and a schematic showing the respective nodes and connecting arms of the design, respectively.
FIG. 5D is a photograph showing deformation of the mesh shown in FIG. 5B.
Figure 6:
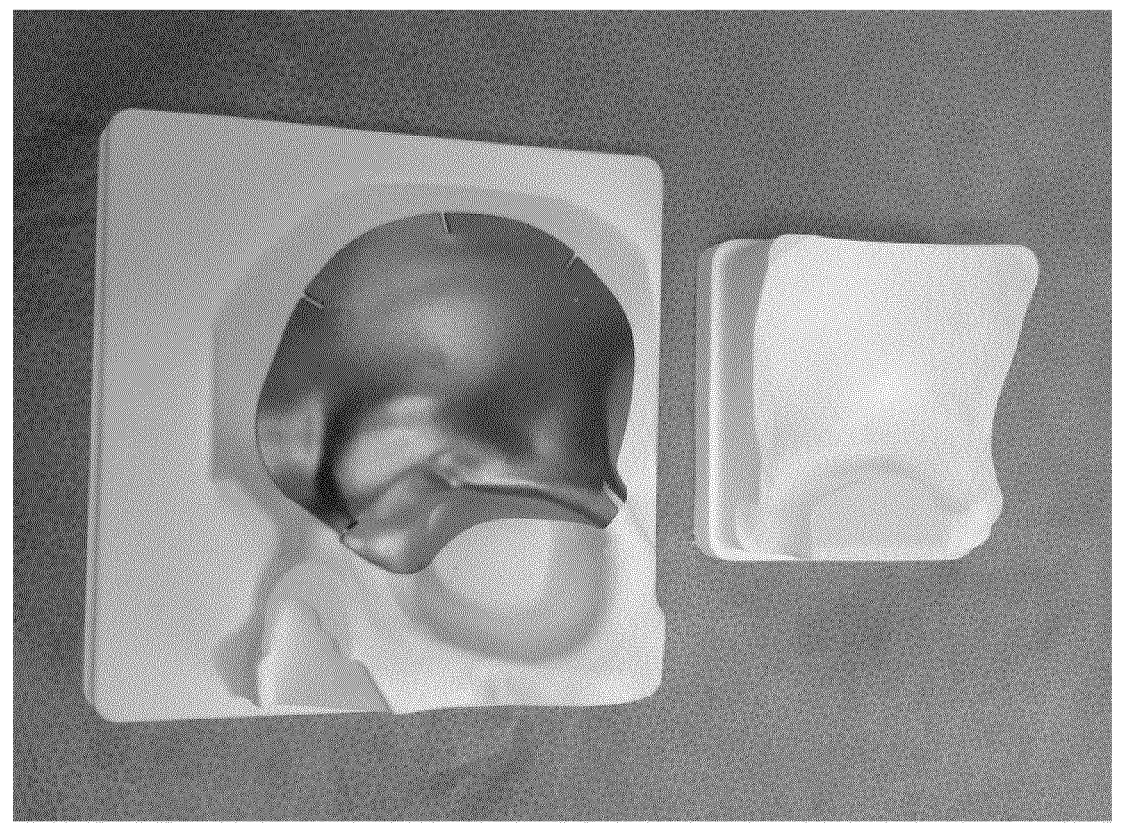
FIG. 6 is a photograph of a solid metallic implant, and a mold system employed to deform the implant.
Figure 7A:
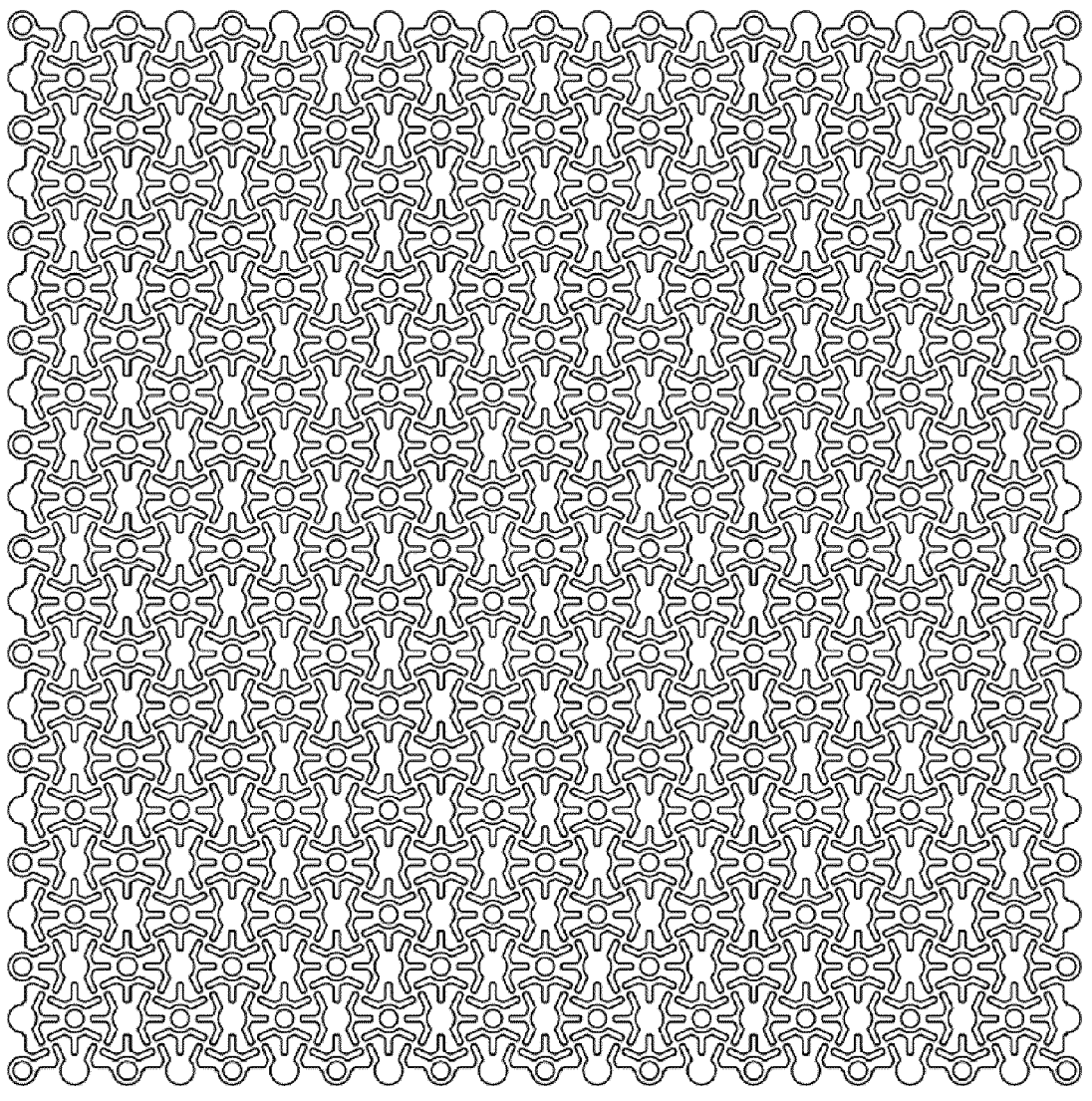
FIG. 7A is an illustration of a mesh for correcting a skeletal defect.

FIG. 7A shows an illustration of an example mesh that addresses the deficiencies of conventional mesh designs. FIG. 7C shows a detailed view of the example mesh, indicating a unit cell of the mesh via line 200. The mesh includes a plurality of node plates that define a lattice (a square lattice in the present non-limiting example), where FIG. 7C shows node plates 200A-200I. At least a subset of the node plates includes respective screw-receiving apertures for receiving mounting screws there through. In the present example implementation, node plate 200E includes a screw-receiving aperture.

As can be seen from FIGS. 7A and 7C, the present mesh has several distinguishing features that differential the mesh relative to the conventional mesh designs described above, as well as addressing the problems associated with the conventional mesh designs that are cited above. For example, as described in further detail below, the example mesh has a higher fill factor (two-dimensional density of mesh material area relative to total area, when viewed from above) than conventional mesh designs, resulting in a more rigid mesh that provides an improved balance between mesh rigidity and mesh transparency, resulting in improved strength and impact resistance while still permitting the viewing of the tissue below the mesh when it is implanted.

The example mesh also exhibits an altered geometrical configuration that avoids the limitations associated with conventional mesh designs that employ a single connecting arm between neighboring nodes. One distinguishing feature of the present example mesh is the absence of direct connections between neighboring node plates. For example, FIG. 7C shows a central node plate 200E surrounded by four nearest-neighbor node plates 200A-200B in a square lattice. A set of connecting arms 205E1-205E4 extend from the central node plate 200E. However, unlike the conventional mesh designs described above, instead of connecting directly with other node plates, each of these connecting arms (205E1-205E4) extends to a respective intermediate connection region, where each intermediate connection region is absent of a screw-receiving aperture. Specifically, connecting arm 205E1 extends to intermediate connection region 225A, connecting arm 205E2 extends to intermediate connection region 225B, connecting arm 205E3 extends to intermediate connection region 225C, and connecting arm 205E4 extends to intermediate connection region 225D. In some example embodiments, the area of each intermediate connection region is smaller than the area of each node plate. In some example embodiments, the area of any given intermediate connection region within the mesh is smaller than the area of node plate that is adjacent to the given intermediate connection region.

As can be seen in FIG. 7C, a plurality of connecting arms meet and connect at each intermediate connection region, where, in the present example embodiment, each connecting arm that connects at a given intermediate connection region extends from a different a different neighboring node plate, such that nearest neighbor node plates are indirectly connected through multiple connecting arms. For example, connecting arms 205F3, 205B4, 205E1, and 205A2, which are respectively associated with node plates 200F, 200B, 200E and 200A, connect at intermediate connection region 225A. As noted above, each intermediate connection region is absent of a screw-receiving aperture.

In the present example mesh embodiment, each pair of nearest-neighboring node plates (e.g. node plates 200E and 200A, 200E and 200B, 200E and 200C, and 200E and 200D) are connected through two connection paths, as opposed to a single connection path. For example, it is apparent that the connection between central node plate 200E and node plate 200B is facilitated through two connection paths involving two pairs of connecting arms, where each pair of connecting arms involves a connection through a different intermediate connection region. A first connection path involves the pair of connecting arms 205E1 and 205B4, which are themselves connected though intermediate connection region 225A. A second connection path involves the pair of connecting arms 205E2 and 205B3, which are themselves connected though intermediate connection region 225B. This dual connection path aspect of the present example mesh can be contrasted with each of the conventional mesh designs described above, in which only a single connection path extended between any two neighboring node plates.

Furthermore, unlike the conventional mesh designs described above, in which non-nearest-neighbor node plates are only connected through additional node plates, diagonal neighboring node plates are connected in the present example mesh. For example, a connection between central node plate 200E and diagonally neighboring node plate 200F is made by connecting arms 205E1 and 205F3, which are connected via intermediate connection region 225A.

Figure 7B:
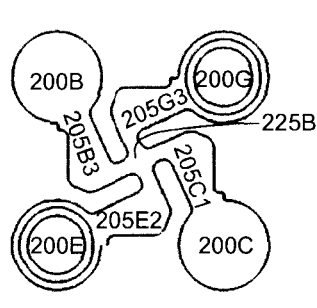
FIG. 7B illustrates the intersection of connecting arms associated with different node plates at an intermediate connection region.
Figure 7C:
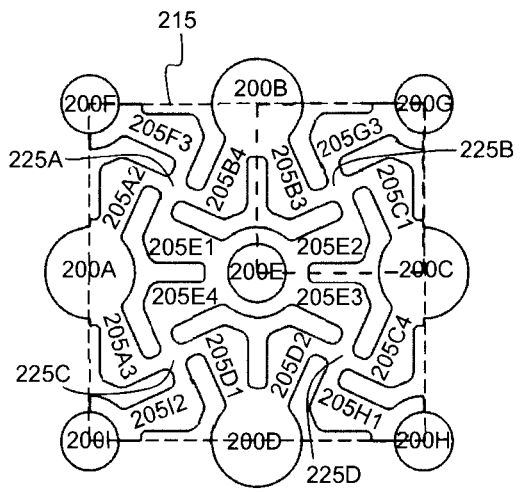
FIG. 7C illustrates a unit cell of the mesh shown in FIG. 7A.
Figure 7D:
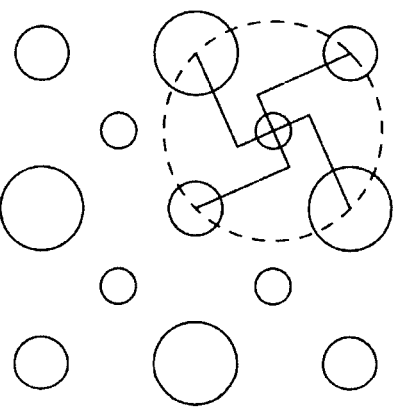
FIGS. 7D and 7E schematically show the connection paths, via the connecting arms, among node plates of the mesh, for the mesh regions illustrated in FIGS. 7B and 7C, respectively.
Figure 7E:
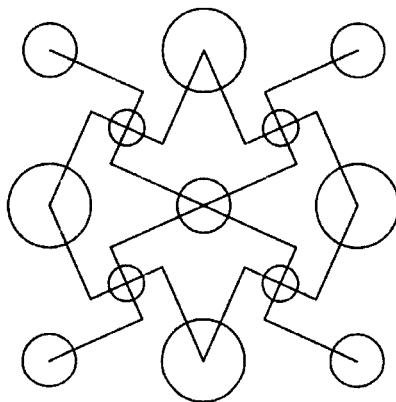

FIGS. 7D and 7E schematically show the connection paths, via the connecting arms, among node plates of the mesh, for the mesh regions illustrated in FIGS. 7B and 7C, respectively.

Referring now to FIGS. 7B and 7D, which show a detailed view and connection path schematic, respectively, of the connecting arms that intersect at a given intermediation connection region, it is apparent that in the example embodiment shown, the connecting arms extending from the given intermediate connection region in a nonlinear configuration, where the connecting arms bend or curve between their connection to a given node plate and a given intermediate connection region. In the example embodiment shown in FIGS. 7B and 7D, the connecting arms extend from the given intermediate connection region in a pinwheel configuration.

Figure 7F:
FIG. 7F is a photograph of an example mesh formed onto a cranial model involving a bilateral frontal defect that includes orbital roof anatomy, where the mesh pattern is based on the unit cell shown in FIG. 7C.

This configuration permits the conversion of a compression force or an expansion force that is applied to the mesh into rotational (e.g. torsional) forces within the mesh. This aspect of the behavior of the mesh is apparent in FIG. 7F, which shows a photograph of a mesh based on the mesh shown in FIG. 7A, where the example mesh in the photograph is formed onto a cranial model, and FIG. 7G, which shows a detailed view of FIG. 7F and indicates the sense of rotation of the pin wheeling structures when a compressive force is applied to the mesh. FIG. 7F demonstrates how the application of force to the mesh results in the rotation of the connecting arms about their respective intermediate connection region, while the node plates may experience little or no rotational motion and instead undergo mainly translational motion (and are thus labeled as being rotationally static in the figure).

As can be seen in FIG. 7G, when a compressive force is applied to the mesh, the connecting arms rotate, relative to the intermediate connection regions (marked by the letter "a" in the figure), torsionally absorbing the applied force the rotational deformation of the mesh. This phenomenon can be further understood with reference to FIGS. 7H and 7I. FIG. 7H shows the configuration of the connecting arms 205133, 205G3, 205C1 and 205E2 that extend from an intermediate connection region 225B in the absence of deformation of the mesh. FIG. 7I shows the effect of a compressive (laterally compressive) force on the mesh. Under the compressive force, the pinwheel structure formed by the connecting arms and the intermediate connection region rotate as the pinwheel structure is compressed laterally. The compression and rotation of the pinwheel structure is shown by the narrowing and angling of box 245 in FIG. 7I relative to box 240 in FIG. 7H.

Moreover, as can be seen in FIG. 7I, the bent connection arms that together, with the intermediate connection region 225B, form the pin wheeling structure, are capable of overlapping with the adjacent node plates during the application of a compressive force. Specifically, connecting arms 205G3 and 205E2 can be seen to be overlapping with the edges of node platforms 200B and 200C, respectively. This aspect of the present example mesh, and other related meshes disclosed herein, is contrary to the conventional mesh designs described above, which all have uniform thickness and are unable to overlap nodes and connecting arms, and are absent of variations in connecting arm cross-sectional geometry.

As the adjacent nodes and connecting arms are forced together, they meet in a similar region of contact throughout the mesh pattern. This is more likely to occur at the perimeter during mesh forming, where areas of high curvature cause parts of the mesh to expand and other areas to contract (as can be seen, for example, in FIG. 7J). To compensate for this distortion, one component of the mesh is enabled to drive over the other in this region, by (i) the design of the pattern, (ii) rounding the edges of the components and (iii) changing the cross-section/material thickness. This creates an interleaving of mesh elements that reduce mesh distortion and strengthen the implant. The overlap of connecting arms and adjacent node plates can be seen FIG. 7J, in which a compressive force applied to the lower region of the mesh during forming of the mesh has caused spatial overlap, thus accommodating the compressive force without causing buckling of the mesh structure.

In some example embodiments, each of the node plates may include a respective screw-receiving aperture. However, in other example embodiments, only a subset of the node plates may include respective screw-receiving apertures. An example of such an embodiment is shown in FIG. 7A, in which half of the node plates include screw-receiving apertures. Reducing the number of screw-receiving apertures in this manner increases the mesh fill factor (density), strength, and impact resistance, while still maintaining a large number of potential locations for fixing the mesh to underlying bone.

In some example embodiments, the mesh may be formed with node plates that have different sized apertures. For example, the node plates may include a first subset of node plates that include respective first apertures having a first diameter, and the node plates may include a second subset of node plates that include second apertures having a second diameter. The first apertures and second apertures may have different diameters. For example, the first subset of node plates may have respective first apertures suitable for receiving a screw (e.g. a bone screw) and the second subset of node plates may have respective second apertures that have a smaller diameter that the first diameter. In such a case, the second apertures of the second subset of node plates may have second diameters that are suitable for the insertion of surgical sutures. The numbers of node plates having the first apertures may differ from the number of node plates having the second apertures. The node plates may include, for example, a third subset of node plates that are absent of apertures. The photograph shown in FIG. 7F shows an example of such a mesh, in which the mesh includes a first subset of node plates having respective first apertures with first diameters suitable for receiving bone screws, a second subset of node plates having respective second apertures with second diameters suitable for the insertion of a surgical suture therethrough, and a third subset of node plates that are absent of apertures.

In some example embodiments, the size of the node plates may vary within the mesh. In some example embodiments, the node plates may be provided in at least two different sizes. While many of the example embodiments shown in the present disclosure employ circular node plate shapes, it will be understood that the circular shape is but one example of a wide variety of possible node plate shapes. For example, in two non-limiting example implementations, the node plate shape may be elliptical or polygonal. In some example embodiments, the node plates defining the lattice may be provided in at least two different shapes.

It will be understood that the preceding example embodiments pertaining to different aperture configurations and node plate shapes and sizes are not intended to be limited to the present example mesh, and can be applied to any mesh. For example, the conventional meshes described above may be adapted according to the preceding example embodiments.

Referring again to FIG. 7C, the connecting arms are shown has having a width that varies over a longitudinal extent thereof. While FIG. 7C shows an example implementation in which all connecting arms have variable widths, this may be case for one or more of the arms in some example implementations. In other example implementations, the widths of one or more of the connecting arms may be constant along the longitudinal extent thereof. In some example embodiments, the width of at least one connecting arm may initially increase towards a maximum width as the connecting arm extends from its respective node plate, and then decrease as the connecting arm extends further to its respective intermediate connection region.

It will be understood that the preceding example embodiments pertaining to width variations of the connecting arms are not intended to be limited to the present example mesh, and can be applied to any mesh. For example, the conventional meshes described above may be adapted according to the preceding example embodiments.

In some example embodiments, the thickness of the mesh may be constant, in a manner similar to conventional mesh designs that have a constant thickness within each unit cell of the mesh, and among unit cells forming the mesh. However, in other example embodiments, the thickness of the mesh may spatially vary within each unit cell of the lattice, and this spatial variation in thickness may be repeated among the unit cells making up the mesh. In other example embodiments, the thickness of the mesh may spatially vary over two or more unit cells of the lattice.

FIGS. 7K-7M illustrate example implementations of a mesh having a thickness variation within a unit cell. FIGS. 7L and 7M show two different example cross-sections based on the cross-section indicated in FIG. 7K. In FIG. 7L, the mesh thickness varies within the central node plate 200E to form a countersunk screw-receiving aperture. In FIG. 7M, an example embodiment is illustrated in which the thickness of the central node plate 200E is different than the thickness of the other node plates 200A and 200C. Furthermore, the thickness of the connecting arm is different than the thicknesses of the node plats. It will be understood that the example implementations shown in FIGS. 7L and 7M are intended to be merely illustrative and non-limiting, and that other variations with different thickness variations may alternatively be implemented. For example, the thickness of one or more connecting arms may additionally or alternatively vary in some example implementations. In some example embodiments, the thickness variations, within a unit cell, may include thickness variations among two or more node plates and/or among one or more connecting arms. In other example embodiments, the thickness variations, within a unit cell, may include thickness variations between the thickness of the connecting arms and the thickness of one or more node plates.

It will be understood that the preceding example embodiments pertaining to thickness variations are not intended to be limited to the present example mesh, and can be applied to any mesh. For example, the conventional meshes described above may be adapted according to the preceding example embodiments.

Figure 7N:
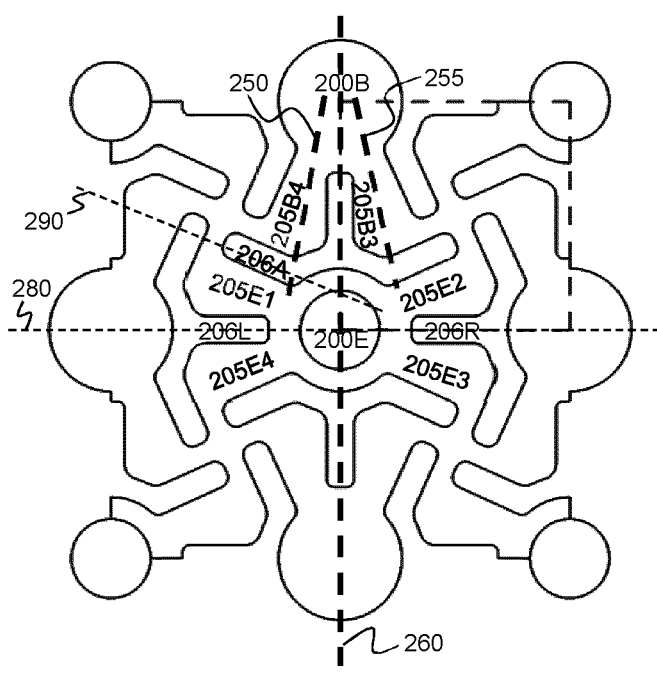
FIGS. 7N and 7O show the differing axial orientations of the connecting arms extending from neighboring node plates.
Figure 7O:
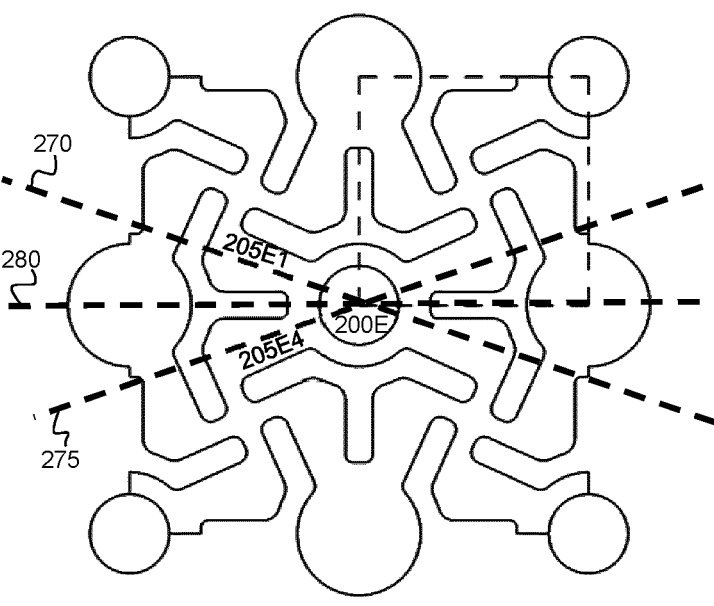
Figure 7P:
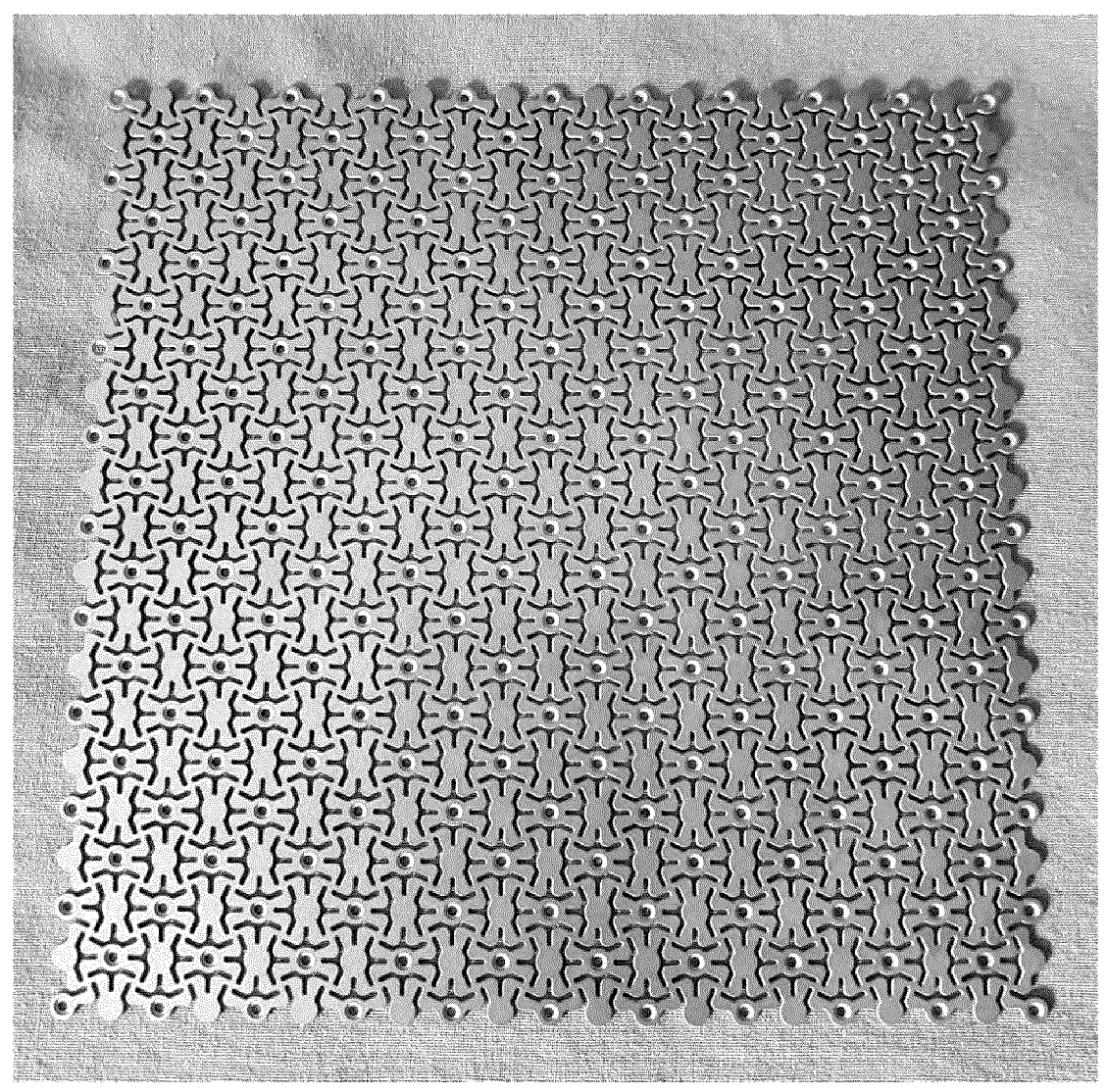
FIG. 7P is a photograph of an example mesh similar to the pattern in 7A, but includes recessed holes for tapered screw heads (e.g.

Referring now to FIGS. 7N and 7O, in the example mesh, the connecting arms of each node plate can be seen to spatially extend from their respective node plates at acute angles relative to a respective alignment axis, with adjacent node plates having different associated alignment axes. For example, as shown in FIG. 7N, connecting arms 205B4 and 205B3 extend downwards, from node plate 200B, along respective directions 250 and 255. These directions lie at acute angles relative to central alignment axis 260 that resides between the two directions. Similarly, as shown in FIG. 7N, the connecting arms 205E1 and 205E4 extend from the central node plate 200E along directions 270 and 275, which lie at acute angles relative to central alignment axis 280. As can be seen comparing FIG. 7N and FIG. 7O, the alignment axes 260 and 280, which are respectively associated with neighboring node plates 200B and 200E, extend in different directions. In the example implementation shown, the two alignment axes 260 and 280 are perpendicular. It is noted that this perpendicular relationship is not intended to be limiting, and the alignment axes associated with neighboring node plates may extend in different directions for different lattice types.

Referring again to FIG. 7N, and considering central node plate 200E, it can be seen that the connecting arms are provided as pairs of adjacent connecting arms that are located on opposing sides of each node plate. For example, a first pair of connecting arms 205E1 and 205E4 lies on the left side of the central node plate 200E, and a second pair of connecting arms 205E2 and 205E3 lie on the right side of the central node plate 200E. As shown in the figure, an inter-arm slot is defined between each pair of connecting arms, where a first inter-arm slot 206L is defined between the connecting arms 205E1 and 205E4, and a second inter-arm slot 206R is defined between the connecting arms 205E2 and 205E3. These inter-arm slots 206L and 206R are useful in defining a deformation (e.g. pivot) axis that lies along the aforementioned alignment axis 280 of the mesh. As can be seen in the figure, the inter-arm slots associated with neighboring node plates extend in different directions, providing different local deformation axes for the mesh.

It is also noted that additional inter-arm slots lie between pairs of connecting arms associated with neighboring node plates. For example, an additional inter-arm slot 206A lies in the region between connecting arm 205E1 that is associated with node plate 200E and connecting arm 205B4 that is associated with node plate 200B. These additional inter-arm slots help to define additional deformation axes, such as axis 290, that lie at oblique angles relative to the aforementioned alignment axes that are associated with pairs of connecting arms that extend from respective node plates.

Referring now to FIGS. 8A-8D, an alternative implementation of the embodiment illustrated in FIGS. 7A-7C is shown, in which the mesh pattern forms a hexagonal lattice as opposed to a square lattice. Accordingly, in the embodiment shown in FIGS. 8A-8C, each intermediate connection region has three connecting arms extending therefrom, as opposed to four connecting arms as in the mesh shown in FIGS. 7A-7C. In the hexagonal mesh, each node plate has three connecting arms extending therefrom, where the connecting arms extend from each node plate in a direction that is radially offset.

It will be understood that the lattice configurations of the example meshes disclosed herein are not intended to be limiting, and that the example mesh can be adapted according to a wide variety of lattice types. Other non-limiting examples of lattice types include rhombohedral, rectangular, and a parallelogram-based lattice.

Figure 9A:
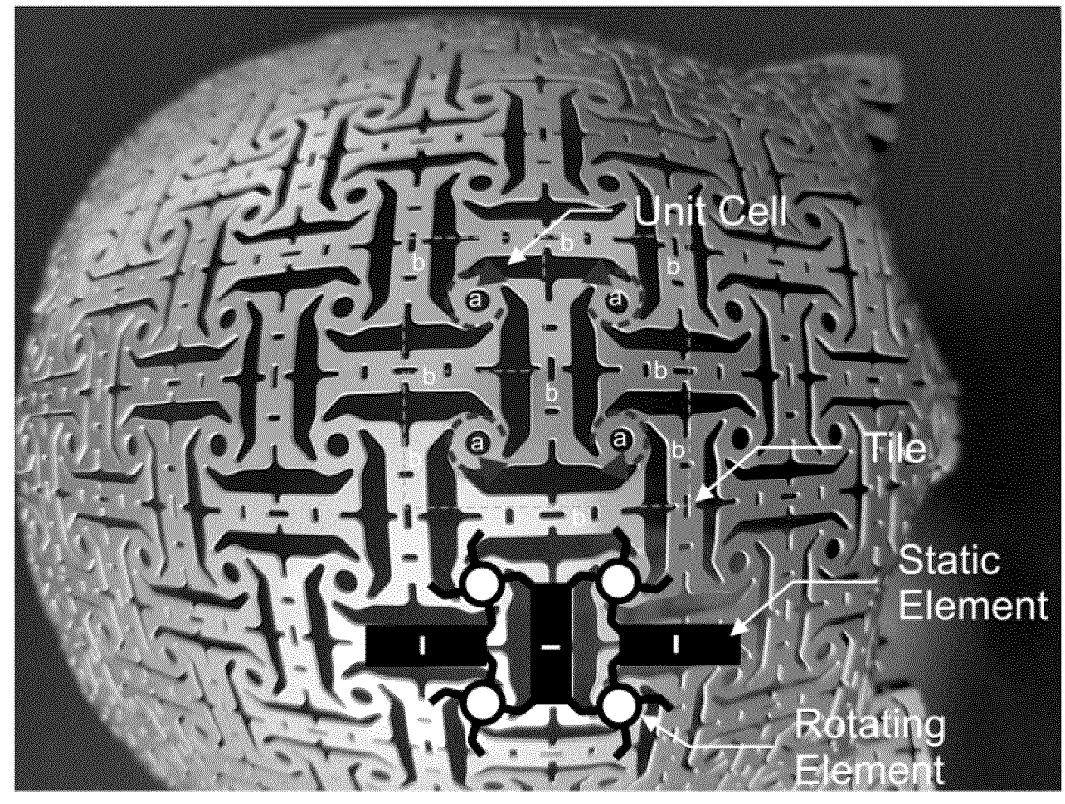
FIG. 9A is a photograph of an alternative example implementation of a mesh pattern.

Referring now to FIG. 9A, a photograph is shown of an example mesh that employs a square lattice of node plates that are interconnected via elongate members. As can been seen in the figure, the present example mesh is absent of direct connections between neighboring node plates, similar to the mesh shown in FIG. 7A.

Figure 9B:
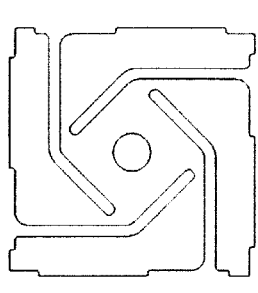
FIG. 9B illustrates the intersection of connecting arms associated with different node plates at an intermediate connection region.
Figure 9C:
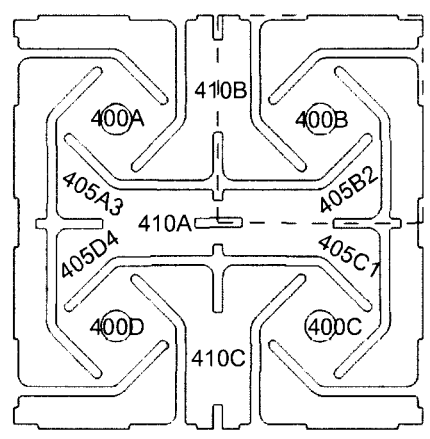
FIG. 9C illustrates a unit cell of the mesh shown in FIG. 9A.

As shown in FIG. 9C, a set of connecting arms extend from the each node plate, such as node plates 400A-400D. However, unlike the conventional mesh designs described above, instead of connecting directly with other node plates, each of these connecting arms extends to a respective elongate member, such as elongate member 410 (which provides an intermediate connection region for the mesh), where, in the embodiment shown in FIGS. 9A and 9C, each elongate member is absent of a screw-receiving aperture. Specifically, connecting arms 405A3, 405B2, 405C1, and 405D4 extends to elongate member 410. As can be seen in FIGS. 9A and 9C, adjacent elongate members are oriented at different angles, and in the present example implementation, the adjacent elongate members are perpendicular, such as adjacent elongate member pairs 410A-410B and 410A-410C.

In the present example mesh embodiment, each pair of nearest-neighboring node plates (e.g. node plates 400A and 400B, 400A and 400D, 400B and 400C, and 400C and 400D) are connected through two connection paths, as opposed to a single connection path. For example, it is apparent that the connection between node plate 400A and node plate 400B is facilitated through two connection paths involving two pairs of connecting arms. A first connection path involves the elongate member 410A, while a second connection path involves the elongate member 410B. This dual connection path aspect of the present example mesh can be contrasted with each of the conventional mesh designs described above, in which only a single connection path extended between any two neighboring node plates.

Furthermore, unlike the conventional mesh designs described above, in which non-nearest-neighbor node plates only connected through additional node plates, diagonal neighboring node plates are connected in the present example mesh. For example, a connection between node plate 400A and diagonally neighboring node plate 400C is made by connecting arms 405A3 and 405C1, which are connected via elongate member 410A.

Figure 9D:
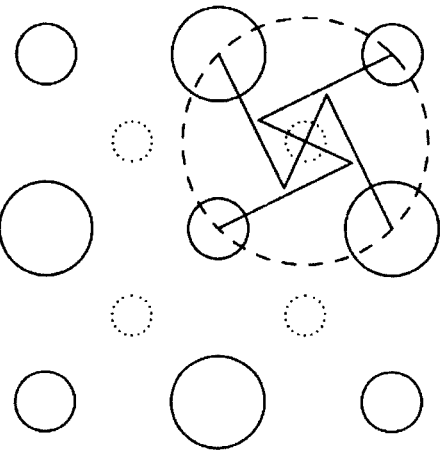
FIGS. 9D and 9E schematically show the connection paths, via the connecting arms, among node plates of the mesh, for the mesh regions illustrated in FIGS. 9B and 9C, respectively.
Figure 9E:
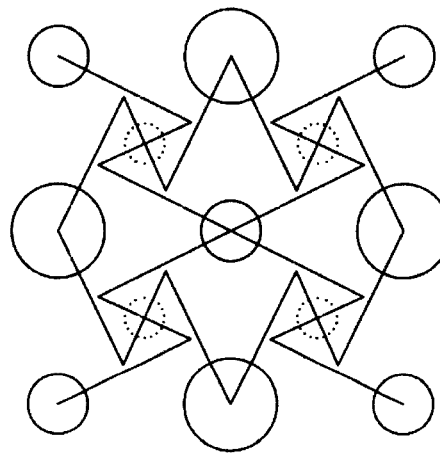

FIGS. 9D and 9E schematically show the connection paths, via the connecting arms, among node plates of the mesh, for the mesh regions illustrated in FIGS. 9B and 9C, respectively.

Figure 9F:
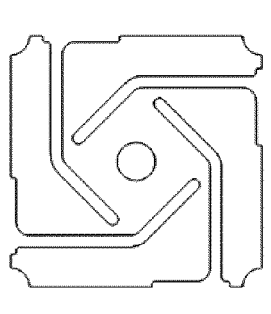
FIGS. 9F and 9G show an alternative mesh configuration including a screw receiving aperture in the elongate mesh members, where
Figure 9G:
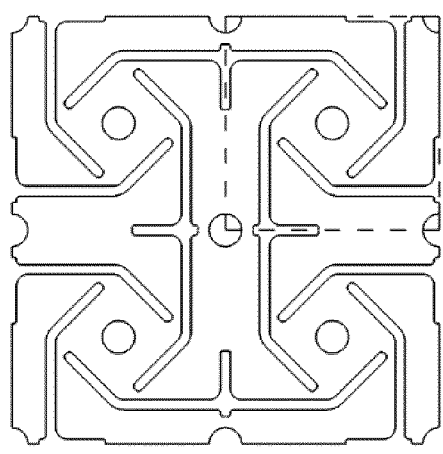

FIGS. 9F and 9G show an alternative example mesh design in which the elongate members include screw-receiving apertures. It will be understood that in alternative example embodiments based on this mesh design, a subset of the elongate members may include screw-receiving apertures.

In the present example implementation, each node plate includes a screw-receiving aperture, but it will be understood that other implementations may be realized in which only a subset of the node plates include respective apertures.

In some example embodiments, one or more elongate members of the mesh may include at least one pair of slots that define a local deformation axis. For example, in the example implementation shown in FIGS. 9A and 9C, each elongate member includes two pairs of perpendicular slots to permit deformation thereof (e.g. during compression of the mesh), where each pair has a respective deformation axis.

FIGS. 10A-10D illustrate another example mesh that differs in topology from the meshes shown in FIGS. 7A, 8A and 9A. Referring to FIG. 10B, the example mesh includes plurality of node plates that define a lattice. The example mesh shows a subset of node plates as including a screw-receiving aperture, although the configuration of may be varied as described above (e.g. employing different subsets of node plates with different sized apertures, or absences of apertures). In the present mesh design, a plurality of connecting arms extends from each node plate, but unlike the mesh designs shown in FIGS. 7A, 8A and 9A, each connecting arm of a given node plate connects with an adjacent node plate without requiring an intermediate connection region.

Instead, and in contrast to the conventional mesh designs described above, nearest-neighbor node plates are directly connected through multiple connecting arms. For example, node plates 500A and 500B are directly connected by connecting arms 505AB1 and 505AB2. While the present example embodiment illustrated in FIG. 10B shows a configuration in which nearest-neighbor node plates are connected through a pair of connecting arms, it will be understood that alternative implementations may be achieved in which nearest-neighbor node plates are connected through three or more connecting arms.

As can be seen in FIG. 10B, in the present example embodiment, each pair of connecting arms that extend between a pair of nearest-neighbor node plates are separated by a pair of intersecting linear slots formed therebetween, such as slots 506AB1 and 506AB2 formed between connecting arms 505AB1 and 505AB2. These intersecting linear slots, which may be perpendicular as shown, or intersecting at an oblique angle, provide local deformation axes to support the deformation of the mesh during the forming of the mesh.

Figure 11A:
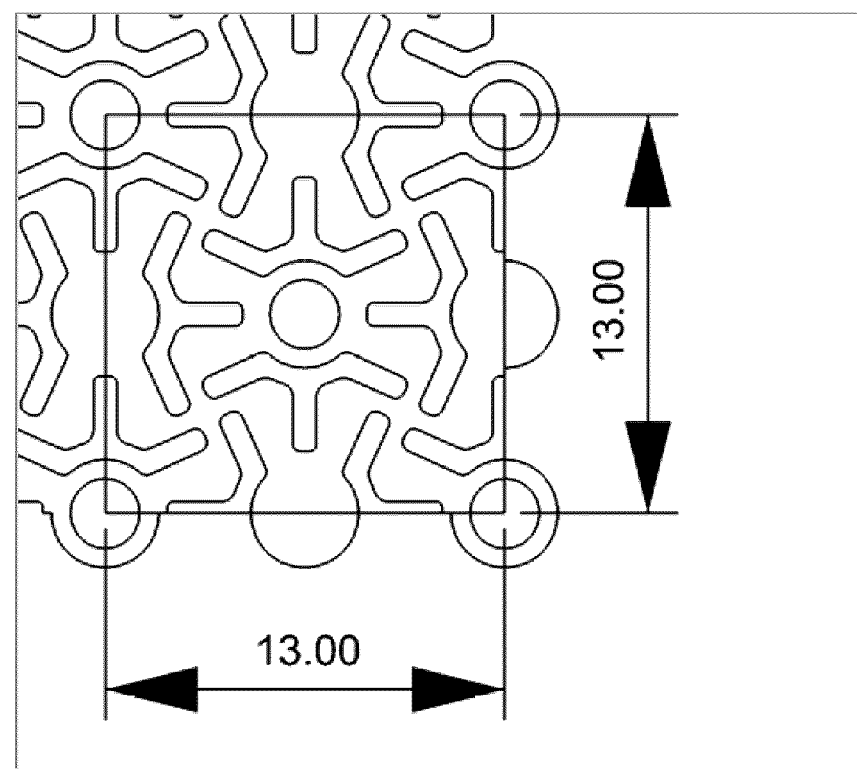
FIG. 11A is an illustration of a portion of the mesh shown in FIG. 7A, illustrating example dimensions of a unit cell.

It will be understood that the meshes disclosed herein may be formed according to the methods and apparatus disclosed in U.S. Pat. No. 8,974,535, titled "METHOD OF FORMING PATIENT-SPECIFIC IMPLANT", which is incorporated herein by reference in its entirety. For example, the meshes may be formed to have features suitable for indexing with the forming tool(s) as per the teachings of U.S. Pat. No. 8,974,535 to provide a custom shaped implant. Furthermore, anatomical features and/or artificial features provided in the mold system, as per the teachings of U.S. Pat. No. 8,974,535, may be employed to facilitate local deformation of template/mesh where the mesh pattern and template geometry are optimized and match. It is also noted that the mold geometry and indexing can be used as a reference guide to locate and position the implant once shaped. As explained above, the example mesh embodiments described herein, and variations thereof, may be employed to achieve higher fill-factor (density) meshes that may provide improved strength relative to conventional mesh designs. A comparison of the fill factor of various meshes is provided in FIGS. 11A-H. FIG. 11A illustrates a portion of the mesh pattern shown in FIG. 7A, where a unit cell is shown having example dimensions of 13×13 mm. As shown in FIG. 11H, a solid implant having these dimensions would have an area of 169 mm$^2$. FIGS. 11B and 11C show the Stryker mesh, having a mesh area of 57.59 mm$^2$ and a fill factor (density) of only 34%. FIG. 11D shows the mesh initially shown in FIG. 7A, having a mesh area of 108 mm$^2$ and a fill factor 64%, which is almost double that of the Stryker mesh. Indeed, the fill factor of the mesh shown in FIG. 11D nearly exceeds the fill factor of the inverse of the Stryker mesh, as can be seen by comparing FIG. 11D and FIGS. 11E-11F. Comparing FIGS. 11G and 11B, it can be seen that the inverse of the mesh shown in FIG. 11D has a fill factor that is close the fill factor of the Stryker mesh.

It will be understood that the mesh designs of the present disclosure may be implemented with a wide range of fill factors (e.g. by varying the size of the mesh features, such as the size of the node plates, the diameter of apertures formed in the node plates, and the length and width of the connecting arms). In some example embodiments, a mesh may be formed according having an area fill factor of at least 0.4, or at least 0.5, or at least 0.6. In some example embodiments, a mesh may be formed according having an area fill factor of between 0.4 and 0.9, or between 0.5 and 0.8, or between 0.6 and 0.7.

In some example embodiments, mesh templates may be provided that are specific to one or more anatomical regions. In other words, a mesh template may be provided, in a flattened state, that has a peripheral shape and/or mesh pattern that is specifically adapted for use with a selected anatomical region. Such region specific mesh templates may include additional features, such as indexing tabs and other markings that assist in the referencing and/or orientation of the mesh, once formed into a suitable shape, relative to patient anatomy.

Figure 12:
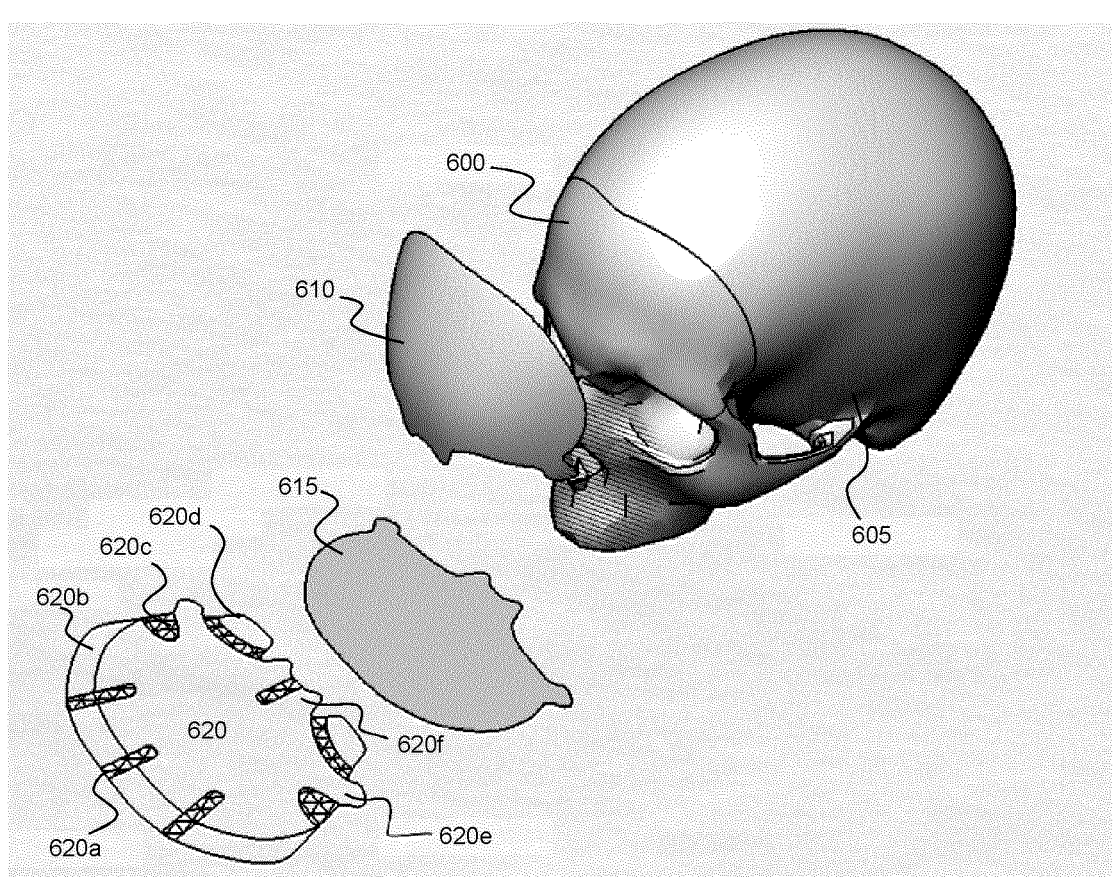
FIG. 12 is an illustration showing how region-specific templates for skull defects can be created using a computerized average skull model, where the regions can be flattened and used to define the boundaries of the proposed mesh pattern. The mesh template can be optimized to include regions that match anatomical features and enhance shaping and implant fixation.

Referring now to FIG. 12, an illustration is provided showing an example implementation of how an anatomical region-specific template for skull defects can be created. In one example implementation, an anatomical region-specific template may be designed using a computerized average skull model. The regions can be flattened and used to define the boundaries of the mesh pattern. The mesh template can be optimized to include regions that match anatomical features and enhance shaping and implant fixation. In FIG. 12, a bilateral frontal defect shape is shown at 600 on a computerized average skull model 605. The average skull is created using the averaging algorithm and 3D process as described in a recent paper by Teshima T L, Patel V, Mainprize J G, Edwards G, and Antonyshyn O M (*A three-dimensional statistical average skull: Application of biometric morphing in generating missing anatomy*, J Craniofac Surg. 2015 July; 26(5):1634-8) and also in a book chapter by Antonyshyn O, Mainprize J, Edwards G. (*Computer Planning for Craniofacial Surgery*. In: Alex M. Greenberg, editor(s). Digital Technologies in Craniomaxillofacial Surgery. (United States): Springer Verlag; 2015, currently in press). In this non-limiting method a library of boney 3D surfaces extracted from skull CT volumes are landmarked by a semi-automatic method. These landmark sets are co-registered together by a generalized procrustes analysis (non-rigid) and a consensus (averaged) landmark set is determined. An average skull surface can be created by morphing (warping) one or more of the skull surfaces to the consensus. The average skull of the whole library or subsets of the library may be used for implant development.

Figure 15A:
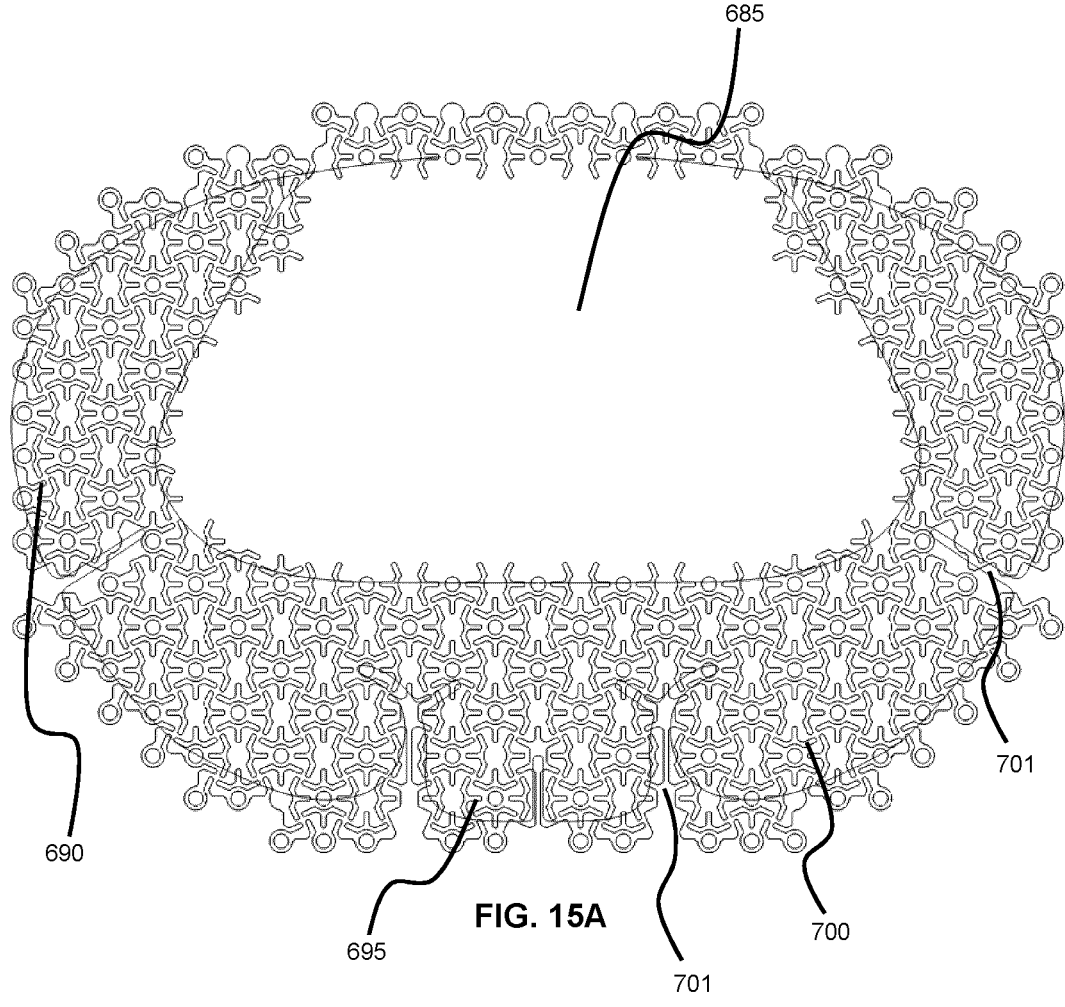
FIG. 15A illustrates how a template can be further improved to include split links and filled regions in various combinations. Such improvements further reduce surface porosity and allow for template regions to adapt to underlying anatomy as required. This example embodiment shown is for a bilateral frontal defect similar to what is shown in FIG. 12.
Figure 15B:
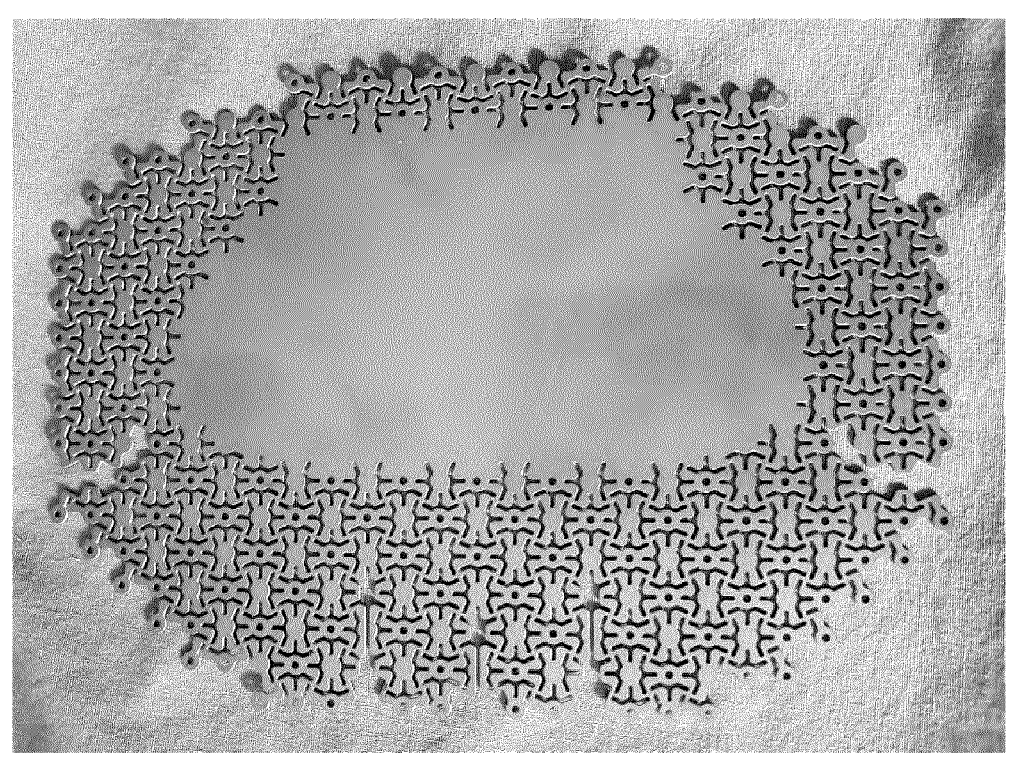
FIG. 15B is a photograph of the example mesh pattern shown in FIG. 15A.
Figure 15C:
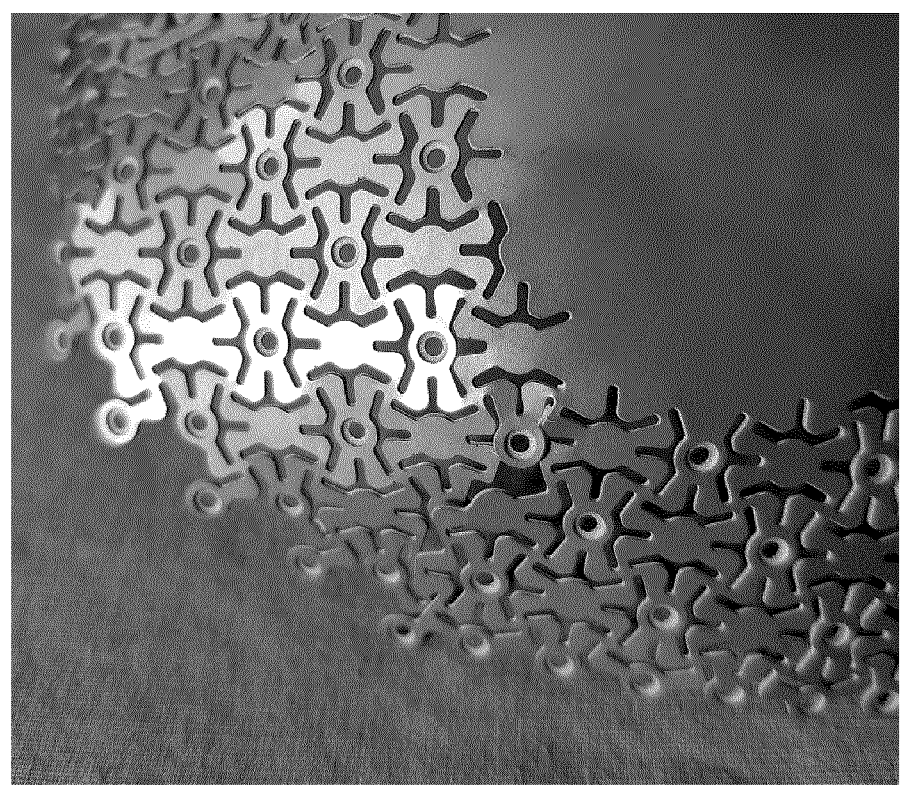
FIG. 15C is a detail photograph of the example mesh shown in FIG. 15B showing implant curvature, solid to pattern transition, mesh interleaving and overlapping.

Cranial defects comprise any full thickness defect of the frontal, parietal, temporal or occipital skull which are known and defined preoperatively or not and which involve the paranasal sinuses or not. A skull database can be used to identify and organize recurring defect types. The average skull model and skull database are used to define a range of defect sizes for a given anatomical region and to develop a mesh size and shape to accommodate the defect geometry. A series of defect templates can then be made for any given region by unfolding and/or flattening the geometry for planar mesh sheets. This is achieved using software that can simulate the unfolding or flattening with finite element analysis and adaptive meshing algorithms (Tri-D Technologies, Toronto, Canada) or with computer-aided design software that can calculate and approximate developable surfaces. The final process includes the manual verification of the 2D template shape on 3D physical models. A bilateral frontal defect region derived from the average skull model and skull database is shown at 610. The mesh template, in its flattened form, is shown at 615. As shown at 620, and explained in further detail below, the anatomical region-specific mesh template may include optimized regions for molding, shaping to anatomical features, and fixation. For example, 620 shows a region that comprises the majority of the template which could be patterned, for example, as shown in FIG. 7F or FIGS. 15A and 15B. The density of the pattern can be adjusted as required, including increasing the fill factor to 1.0. Element 620*a* indicates a change in the mesh pattern to enhance folding of the mesh where the implant needs to bow outward to match the desired shape from skull apex to brow. An example of a detail of this enhancement is shown in FIG. 15C. Element 620*c* shows a change in mesh pattern and/or density to allow for a local concavity, the posterior aspect of the frontozygomatic suture. This coincides with the feature shown in 620*e* to conform to the zygomatic process of frontal bone. Another series of features are identified in 620*d*, the upper orbital rim and orbital roof and 620*f*, glabella and nasal bone. As shown by element 620*b*, a variable region or band can be added to modify and incrementally increase the size of the template around the perimeter. This region would also contain the majority of fixation points for the implant.

Figure 13:
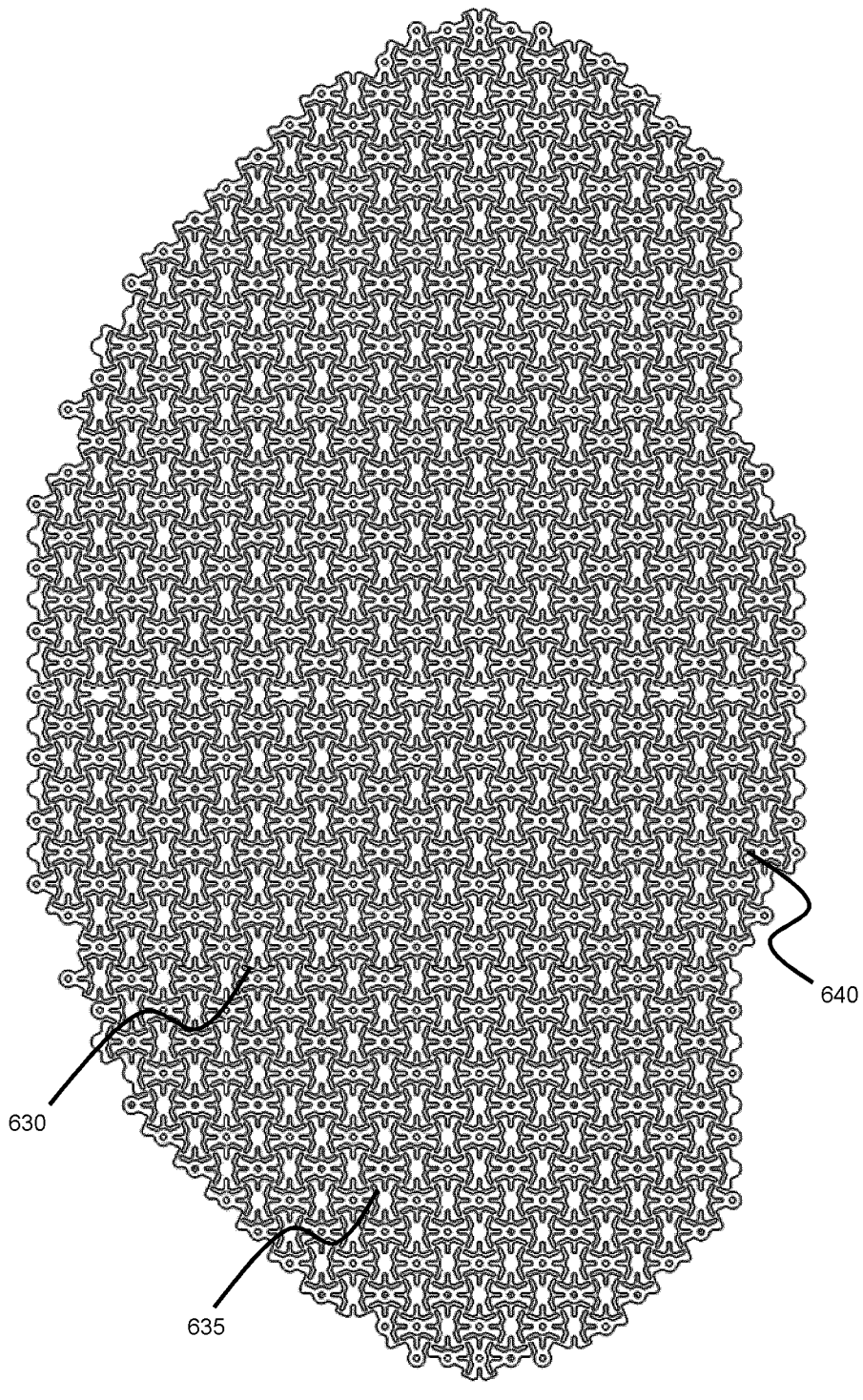
FIG. 13 shows a flattened template for a bilateral cranial defect. Once folded and shaped, it will form a patient specific restoration of the defect. It is noted that holes can be deleted and added as required to provide fixation points.

FIG. 13 shows an example of a flattened template for a bilateral cranial defect. Once folded and shaped, it will form a patient specific restoration of the defect. It is noted that holes can be deleted and added as required to provide fixation points. As shown in the figure, the flattened anatomical region-specific mesh template includes a frontal flap over a sinus feature 640, an implant region 630 for a large bilateral cranial defect, and a temporal/parietal flap feature 635.

Figure 14A:
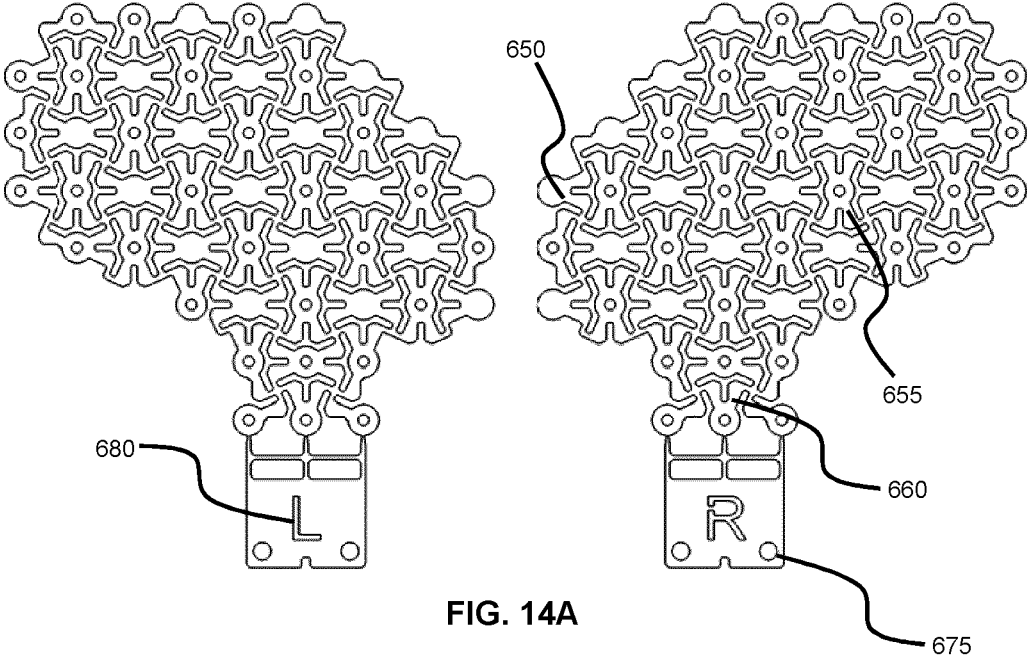
FIGS. 14A and 14B show templates for orbital floor defects using the example pattern from FIG. 7, where
Figure 14B:
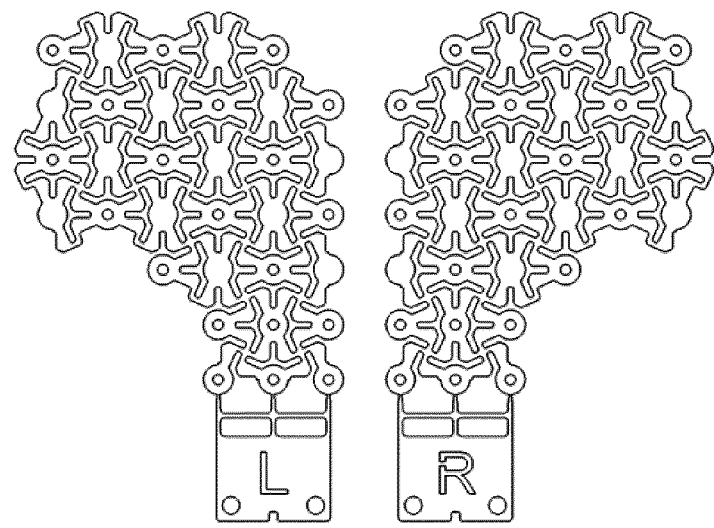
Figure 14C:
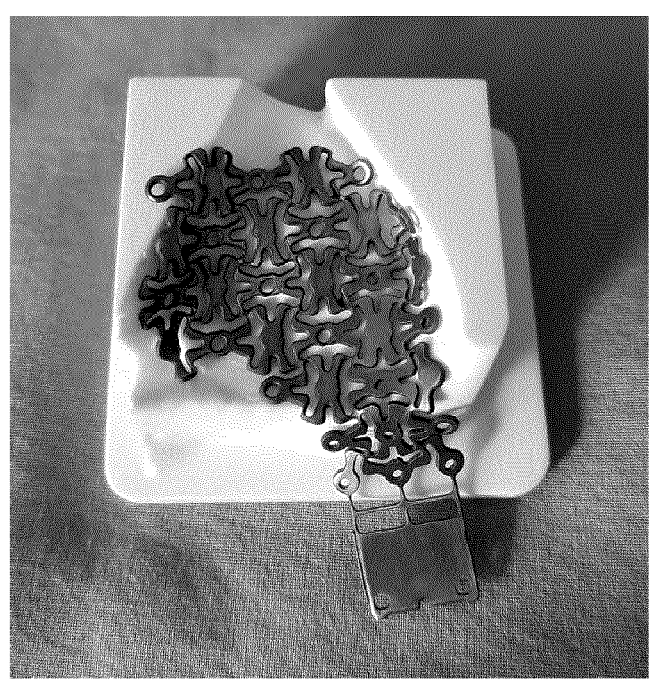
FIGS. 14C and 14D show photographs of the example mesh in FIG. 14B after shaping to an anatomical mold and placed in an anatomical orbital defect model. Mesh restores defect to pre-injury shape and conforms to existing anatomy.
Figure 14D:
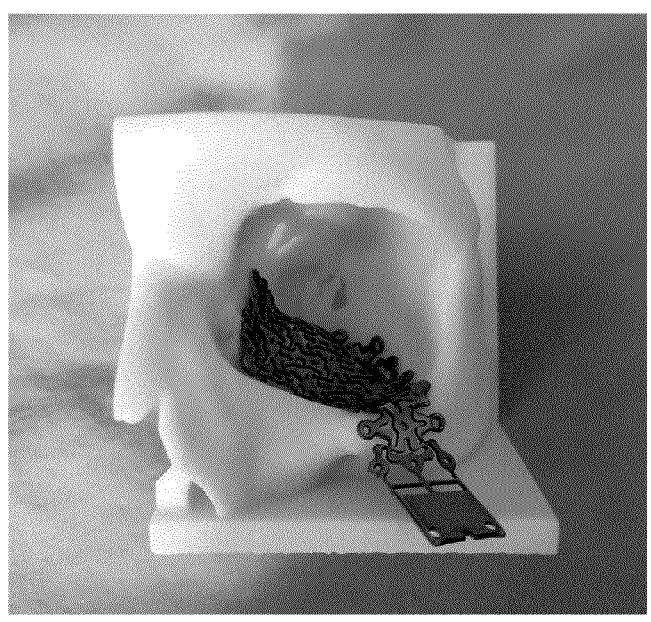

FIGS. 14A and 14B show anatomical region-specific mesh templates for orbital floor defects using the example pattern from FIG. 7, where FIG. 14A shows left and right patterns for orbital floors that include both lateral and medial walls, and FIG. 14B shows left and right patterns for orbital floor and medial wall only. The example orbital floor templates shown in the FIG. 14A include a lateral wall feature 650, a medial wall feature 655, an anatomical indexing flap 660, a mold indexing feature 675, and an identifying feature 680. It will be understood that orbital floor templates may include any or all of these features. The example orbital floor templates shown in FIG. 14B are absent of the lateral wall feature. FIGS. 14C and 14D show photographs of the example mesh in FIG. 14B after shaping to an anatomical mold and placed in an anatomical orbital defect model. Mesh restores defect to pre-injury shape and conforms to existing anatomy.

FIG. 15A illustrates an example of anatomical region-specific bilateral frontal defect that is modified to include additional features, such as split links and/or filled regions, which may be included in various combinations. In the example implementation shown in FIG. 15A, the anatomical region-specific mesh template includes features such as a solid frontal panel feature 685 that is absent of mesh links and voids, a temporal feature 690, a nose/glabella feature

695, and a supraorbital feature 700. Such improvements
further reduce surface porosity and allow for template
regions to adapt to underlying anatomy as required. The
shaping of these regions can be enhanced by introducing
slots 701, an absence of pattern 701, or a change in mesh density. Each panel can bend freely, conform to patient
specific anatomy and allow the surgeon to edit the template
as required.

FIG. 15B is a photograph of the example mesh pattern
shown in FIG. 15A, while FIG. 15C is a detail photograph
of the example mesh shown in FIG. 15B showing implant
curvature, solid to pattern transition, mesh interleaving and
overlapping.

The specific embodiments described above have been
shown by way of example, and it should be understood that
these embodiments may be susceptible to various modifi-
cations and alternative forms. It should be further under-
stood that the claims are not intended to be limited to the
particular forms disclosed, but rather to cover all modifica-
tions, equivalents, and alternatives falling within the spirit
and scope of this disclosure.

THEREFORE WHAT IS CLAIMED IS:

1. A formable implant for skeletal fixation or correction of
skeletal defects, the formable implant comprising a formable
mesh region, the formable mesh region comprising:
a plurality of node plates spatially arranged according to
     a two-dimensional lattice;
   wherein each of the plurality of node plates is surrounded
     by a plurality of intermediate connection structures that
     provide connections between the respective node plate
and a set of neighbouring node plates of the plurality of
     node plates;
   each of the plurality of intermediate connection structures
     comprising a plurality of connecting arms that extend
     outwardly in a pinwheel configuration, such that each
connecting arm of the plurality of connecting arms
     connects with one respective node plate of the plurality
     of node plates, the plurality of connecting arms being
     configured such that when a lateral compressive force
     is applied within the formable mesh region, the laterally applied compressive force is converted into tor-
     sional forces, and the laterally applied compressive
     force is torsionally absorbed via rotation of the plurality
     of intermediate connection structures while the node
     plates remain rotationally static.

2. The formable implant according to claim 1 wherein
each of the plurality of node plates comprises an elongate
member.

3. The formable implant according to claim 2 wherein
adjacent ones of the elongate members are oriented at different angles.

4. The formable implant according to claim 3 wherein
adjacent ones of the elongate members are perpendicular to
each other.

5. The formable implant according to claim 2 wherein
each of the elongate members comprises at least one pair of
slots defined therein to permit deformation thereof.

6. The formable implant according to claim 1 wherein
nearest-neighboring node plates of the plurality of node
plates are connected through two of the plurality of intermediate connection structures.

7. The formable implant according to claim 1 wherein at
least one connecting arm of the plurality of connecting arms
has a width that varies over a longitudinal extent thereof.

8. The formable implant according to claim 1 wherein a
width of at least one connecting arm of the plurality of
connecting arms initially increases towards a maximum width as the at least one connecting arm initially extends
toward a respective node plate of the plurality of node plates,
and then decreases as the at least one connecting arm
extends further toward the respective node plate of the
plurality of node plates.

9. The formable implant according to claim 1 wherein
each node plate of the plurality of node plates has a
respective screw-receiving aperture.

10. The formable implant according to claim 1 wherein a
first subset of the plurality of node plates have respective
screw-receiving apertures, and wherein the plurality of node
plates comprises a second subset of the plurality of node
plates that are absent of screw-receiving apertures.

11. The formable implant according to claim 1 wherein a
first subset of the plurality of node plates have respective
screw-receiving apertures, and wherein the plurality of node
plates comprises a second subset of the plurality of node
plates that have respective additional apertures defined
therein, wherein the diameters of the additional apertures are
smaller than the diameters of the screw-receiving apertures.

12. The formable implant according to claim 11 wherein
the diameters of the additional apertures are suitable for
inserting a surgical suture therethrough.

13. The formable implant according to claim 11 wherein
the plurality of node plates comprises a third subset of the
plurality of node plates that are absent of apertures.

14. The formable implant according to claim 1 wherein an
area fill factor of the formable mesh region is at least 0.4.

15. The formable implant according to claim 1 wherein an
area fill factor of the formable mesh region is at least 0.5.

16. The formable implant according to claim 1 wherein an
area fill factor of the formable mesh region is at least 0.6.

17. The formable implant according to claim 1 wherein a
thickness of the formable mesh region spatially and repeat-
ably varies over each unit cell of the lattice.

18. The formable implant according to claim 1 wherein a
thickness of the formable mesh region spatially varies over
two or more unit cells of the lattice.

19. The formable implant according to claim 1 further
comprising one or more solid regions that are connected to,
and extend beyond, the formable mesh region.

20. The formable implant according to claim 1 wherein
each of the plurality of intermediate connection structures
includes only three of the plurality of connecting arms.

21. The formable implant according to claim 1 wherein
each of the plurality of intermediate connection structures
includes only four of the plurality of connecting arms.

22. The formable implant according to claim 1 wherein
the plurality of node plates defining the lattice are provided
in at least two different sizes.

23. The formable implant according to claim 1 wherein
the plurality of node plates defining the lattice are provided
in at least two different shapes.

24. A formable implant for skeletal fixation or correction
of skeletal defects, the formable implant comprising a form-
able mesh region, the formable mesh region comprising:
   a plurality of node plates defining a lattice, wherein at
     least a subset of the plurality of node plates comprise
     respective screw-receiving apertures for receiving
     mounting screws therethrough;
   each node plate of the plurality of node plates having a
     plurality of connecting arms extending therefrom, each
     of the plurality of connecting arms extending from a
     given node plate of the plurality of node plates connects
     with an adjacent node plate of the plurality of node
     plates;

19

20 wherein adjacent node plates of the plurality of node plates are directly connected through a pair of the plurality of connecting arms; and wherein each pair of the plurality of connecting arms are separated by a pair of intersecting linear slots formed therebetween in a crossed configuration, each of the linear slots defining and extending along a respective axis.

25. The formable implant according to claim 24 wherein the linear slots of each pair of intersecting linear slots are perpendicular to each other.

*    *    *    *    *